US010258633B2

(12) United States Patent
Fiorucci et al.

(10) Patent No.: US 10,258,633 B2
(45) Date of Patent: *Apr. 16, 2019

(54) TREATMENT OF FIBROSIS USING FXR LIGANDS

(71) Applicants: Stefano Fiorucci, Perugia (IT); Roberto Pellicciari, Perugia (IT); Mark Pruzanski, New York, NY (US)

(72) Inventors: Stefano Fiorucci, Perugia (IT); Roberto Pellicciari, Perugia (IT); Mark Pruzanski, New York, NY (US)

(73) Assignee: Intercept Pharmaceuticals, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/299,559

(22) Filed: Oct. 21, 2016

(65) Prior Publication Data

US 2017/0165277 A1 Jun. 15, 2017

Related U.S. Application Data

(63) Continuation of application No. 11/081,002, filed on Mar. 14, 2005, now Pat. No. 9,498,484.

(60) Provisional application No. 60/552,865, filed on Mar. 12, 2004.

(51) Int. Cl.
*A61K 31/56* (2006.01)
*A61K 31/575* (2006.01)

(52) U.S. Cl.
CPC ............ *A61K 31/575* (2013.01); *A61K 31/56* (2013.01)

(58) Field of Classification Search
CPC combination set(s) only.
See application file for complete search history.

(56) References Cited

U.S. PATENT DOCUMENTS

| | | | |
|---|---|---|---|
| 4,892,868 | A | 1/1990 | Castagnola et al. |
| 4,921,848 | A | 5/1990 | Frigerio et al. |
| 5,061,701 | A | 10/1991 | Pellicciari et al. |
| 5,128,481 | A | 7/1992 | Oda et al. |
| 5,175,320 | A | 12/1992 | Pellicciari et al. |
| 6,200,998 | B1 | 3/2001 | Sahoo et al. |
| 6,559,188 | B1 | 5/2003 | Gatlin et al. |
| 6,639,078 | B1 | 10/2003 | Haffner et al. |
| 6,777,446 | B2 | 8/2004 | Houze et al. |
| 6,906,057 | B1 | 6/2005 | Forman et al. |
| 6,984,650 | B2 | 1/2006 | Haffner et al. |
| 6,987,121 | B2 | 1/2006 | Kliewer et al. |
| 7,138,390 | B2 | 11/2006 | Pellicciari |
| 7,319,109 | B2 | 1/2008 | Boggs et al. |
| 2002/0094977 | A1 | 7/2002 | Robl et al. |
| 2002/0120137 | A1 | 8/2002 | Houze et al. |
| 2002/0132223 | A1 | 9/2002 | Forman et al. |
| 2003/0130296 | A1 | 7/2003 | Bauer et al. |
| 2007/0015796 | A1 | 1/2007 | Jones et al. |

FOREIGN PATENT DOCUMENTS

| | | |
|---|---|---|
| EP | 0101554 A1 | 2/1984 |
| EP | 0124068 A1 | 11/1984 |
| EP | 0135782 A2 | 4/1985 |
| EP | 0186023 A2 | 7/1986 |
| EP | 0312867 A1 | 4/1989 |
| EP | 0393493 A2 | 10/1990 |
| EP | 1378749 A1 | 1/2004 |
| EP | 1473042 A1 | 11/2004 |
| EP | 1568706 A1 | 8/2005 |
| EP | 1947108 A1 | 7/2008 |
| WO | WO-9728149 A1 | 8/1997 |
| WO | WO-9736579 A1 | 10/1997 |
| WO | WO-9802159 A1 | 1/1998 |
| WO | WO-9938845 A1 | 8/1999 |
| WO | WO-2000025134 A1 | 5/2000 |
| WO | WO 2000/37077 A1 | 6/2000 |
| WO | WO-0040965 A1 | 7/2000 |
| WO | WO-2000057915 A1 | 10/2000 |
| WO | WO-2000076523 A1 | 12/2000 |
| WO | WO-0130343 A1 | 5/2001 |
| WO | WO-9731907 A | 6/2001 |
| WO | WO-2002020463 A2 | 3/2002 |
| WO | WO-2002064125 A2 | 8/2002 |
| WO | WO 02/072598 A1 | 9/2002 |
| WO | WO-03015771 A1 | 2/2003 |
| WO | WO-03015777 A1 | 2/2003 |
| WO | WO-03016280 A1 | 2/2003 |
| WO | WO-03016288 A1 | 2/2003 |
| WO | WO-2003030612 A2 | 4/2003 |
| WO | WO 03/043581 A2 | 5/2003 |
| WO | WO-2003080803 A2 | 10/2003 |
| WO | WO-2003086303 A2 | 10/2003 |
| WO | WO-2003090745 A1 | 11/2003 |

(Continued)

OTHER PUBLICATIONS

Stenner et al., Flak Symposium, 2002, pp. 229-235.
Trauner et al., Aliment Pharmacol Ther., 1999; 13, pp. 979-995.
Konstantinos N. Lazaridis et al., Journal of Hepatology, 35, 2001, pp. 134-146.
Jane-L. Lew et al., The Journal of Biological Chemistry, vol. 279, No. 10, pp. 8856-8861.
Roberto Pellicciari, et al., Journal of Medicinal Chemistry, vol. 45, No. 17, 2002, pp. 3569-3572.
John Y.L. Chiang, Journal of Hepatology, 40, 2004, pp. 539-551.
Stefano Fiorucci, et al., Hepatotogy, 39(2), 2004, pp. 365-375.
Opposition filed in corresponding EP application No. 05729394.6, filed Sep. 30, 2015.
Aldini et al., "Relationship between structure and intestinal absorption of bile acids with a steroid or side-chain modification", *Steroids*, 61(10):590-597 (1996).

(Continued)

*Primary Examiner* — Shobha Kantamneni
(74) *Attorney, Agent, or Firm* — Michelle Iwamoto-Fan

(57) ABSTRACT

The present invention relates to a method for inhibiting fibrosis that occurs in an organ where the farnesoid X receptor (FXR) is expressed. This method involves the step of administering a high potency, activating ligand of FXR in an effective amount to a patient who is not suffering from a cholestatic condition. The invention also provides pharmaceutical compositions containing an effective amount of an FXR ligand and kits for dispensing the pharmaceutical compositions.

6 Claims, 8 Drawing Sheets

Specification includes a Sequence Listing.

(56) References Cited

FOREIGN PATENT DOCUMENTS

| WO | WO 2004/007521 | | 1/2004 |
|---|---|---|---|
| WO | WO 2004/048349 | A1 | 6/2004 |
| WO | 2005032549 | | 4/2005 |
| WO | WO 2005/032549 | A1 | 4/2005 |
| WO | WO-2005082925 | A2 | 9/2005 |
| WO | WO-2005089316 | A2 | 9/2005 |
| WO | WO-2006122977 | A2 | 11/2006 |
| WO | WO-2008002573 | A2 | 1/2008 |
| WO | WO-2008091540 | A2 | 7/2008 |
| WO | WO-2010059853 | A1 | 5/2010 |

OTHER PUBLICATIONS

Bishop-Bailey et al., "Expression and activation of the farnesoid X receptor in the vasculature", *Proc. Natl. Acad. Sci. U.S.A.*, 101(10):3668-3673 (2004).

Center, S.A., et al., "Chronic Liver Disease: Current Concepts of Disease Mechanisms", *J. Small Anim. Pract.*, 40(3), 106-114 (1999).

Clerici et al., "Effect of Intraduodenal Administration of 23-Methyl-UDCA Diastereoisomers on Bile Flow in Hamsters", *Dig. Dis. Sci.*, 37(5):791-798 (1992).

Cui et al., "The Amino Acid Residues Asparagine 354 and Isoleucine 372 of Human Farnesoid X Receptor Confer the Receptor with High Sensitivity to Chenodeoxycholate", *J. Bio. Chem.*, 277:25963-25969 (2002).

Downes, M., et al., A Chemical, Genetic, and Structural Analysis of the Nuclear Bile Acid Receptor FXR, *Mol. Cell.*, 11(4), 1079-1092 (2003).

Fukuchi et al., "5beta-Cholane activators of the farnesol X receptor," *Journal of Steroid Biochemistry and Molecular Biology*, 94(4):311-318 (2005).

Goodwin et al., "A Regulatory Cascade of the Nuclear Receptors FXR, SHP-1, and LRH-1 Represses Bile Acid Biosynthesis", *Mol. Cell.*, 6:517-526 (2000).

Haslewood et al., "Specificity and some characteristics of a 7.alpha.-hydroxysteroid dehydrogenase from *E. coli*", Datebase CA [online], Database accession No. 1978:419015.

Honorio et al., "Hologram QSAR Studies on Farnesoid X Receptor Activators", *Lett. Drug Des. Dis.*, 3(4):261-267 (2006).

Jones et al., "Cell-Free Ligand Binding Assays for Nuclear Receptors", *Methods Enzymol.*, 364:53-71 (2003).

Kanda et al., "Regulation of Expression of Human Intestinal Bile Acid-Binding Protein in Caco-2 Cells", *Biochem. J.*, 330:261-265 (1998).

Kihira et al., "Synthesis of sulfonate analogs of bile acids", *Steroids*, 57(4):193-198 (1992).

Kim et al., "Hypocholesterolemic effect of bile acid sulfonate analogs in hamsters", *Biological & Pharmaceutical Bulletin*, 24(3):218-220 (2001).

Kliewer et al., "Peroxisome Proliferator-Activated Receptors: From Genes to Physiology", *Endo J.*, 56:239-263 (2001).

Liu, Y. et al., "Hepatoprotection by the Farnesoid X Receptor Agonist GW4064 in Rat Models of Intra- and Extrahepatic Cholestasis", *J. Clin. Invest.*, 112(11), 1678-1687 (2003).

Lu et al., "Orphan Nuclear Receptors as eLiXiRs and FiXeRs of Sterol Metabolism", *J. Biol. Chem.* 276:37735-37738 (2001).

Makishima et al., "Identification of a Nuclear Receptor for Bile Acids", *Science*, 284:1362-1365 (1999).

Maloney et al., "Identification of a Chemical Tool for the Orphan Nuclear Receptor FXR", *J. Med. Chem.*, 43(16):2971-2974 (2000).

Mangelsdorf et at., "The RXR Heterodimers and Orphan Receptors", Cell, 83:841-850 (1995).

Mi et al., "Structural Basis for Bile Acid Binding and Activation of the Nuclear Receptor FXR", *Mol. Cell*, 11:1093-1100 (2003).

Mikami et al., "Effect of some sulfonate analogs of ursodeoxycholic acid on biliary lipid secretion in the rat", *Journal of Lipid Research:*, 37(6):1181-1188 (1996).

Miki et al., "Sulfonate analogs of chenodeoxycholic acid: metabolism of sodium 3. alpha., 7. alpha.-dihydroxy-25-homo-5. beta.-cholane-25-sulfonate and sodium 3.alpha., 7. alpha-dihydroxy-24-nor-5. beta.-cholane-23-sulfonate in the hamster", *Journal of Lipid Research*, 33(11):1629-1637 (1992).

Nesta et al., "Thiazolidinedione Use, Fluid Retention, and Congestive Heart Failure", *Diabetes Care*, 27(1):256-263 (2004).

Parks et al., "Bile Acids: Natural Ligands for an Orphan Nuclear Receptor", *Science*, 284:1365-1368 (1999).

Pellicciari et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid", *J. Med. Chem.*, 47:4559-4569 (2004).

Pellicciari et al., "Nongenomic Actions of Bile Acids. Synthesis and Preliminary Characterization of 23- and 6,23-Alkyl-Substituted Bile Acid Derivatives as Selective Modulators for the G-Protein Coupled Receptor TGR5", *J. Med. Chem.*, 50:4265-4268 (2007).

Raskin et al., "A Randomized Trial of Rosiglitazone Therapy in Patients With Inadequately Controlled Insulin-Treated Type 2 Diabetes", *Diabetes Care*, 24(7):1226-1232 (2001).

Roda et al., "23-Methyl-3a.,7b-dihydroxy-5b-cholan-24-oic Acid: Dose-Response Study of Biliary Secretion in Rat", *Hepatol.*, 8(6):1571-1576 (1988).

Roda et al., "Bile acids with a cyclopropyl-containing side chain. IV. Physicochemical and biological properties of the four diastereoisomers of 3a,7b-dihydroxy-22,23-methylene-5b-cholan-24-oic acid", *J. Lipid Res.*, 28(12):1384-1397 (1987).

Rubin et al., "Combination Therapy With Pioglitazone and Insulin in Patients With Type 2 Diabetes", *Diabetes*, 48(Suppl. 1):A110 (1999) (Abstract Only).

Sato et al., "Novel Potent and Selective Bile Acid Derivatives as TGR5 Agonists: Biological Screening, Structure-Activity Relationships, and Molecular Modeling Studies", *J. Med. Chem.*, 51(6):1831-1841 (2008).

Schmider et al., "Evidence for an additional sinusoidal bile salt transport system", Datebase CA [online],. Database accession No. 2000:260886, Feb. 16, 2009.

Schwartz et al., "Two 7 Hydroxylase Enzymes in Bile Acid Biosynthesis", *Curr. Opin. Lipidol.*, 9:113-118 (1998).

Souillac et al., "Characterization of Delivery Systems, Differential Scanning Calorimetry", in *Encyclopedia of Controlled Drug Delivery*, John Wiley & Sons, pp. 212-227 (1999).

Urizar, N.L. et al., A Natural Product that Lowers Cholesterol as an Antagonist Ligand for FXR, *Science*, 296(5573), 1703-1706 (2002).

Vippagunta et al., "Crystalline solids", *Adv. Drug Del. Rev.*, 48:3-26 (2001).

Wang et al., "Endogenous Bile Acids are Ligands for the Nuclear Receptor FXR/BAR", *Mol. Cell.*, 3:543-553 (1999).

Willson et al., "The PPARs: From Orphan Receptors to Drug Discovery", *J. Med. Chem.*, 43(4):527-550 (2000).

Fiorucci et al., "The Nuclear Receptor SHP Mediates Inhibition of Hepaptic Stellate Cells by FXR and Protects against Liver Fibrosis", *Gastroenterology*, 127:1497-1512 (2004).

Forman et al., "Identification of a Nuclear Receptor That is Activated by Farnesol Metabolites", *Cell*, 81:687-693 (1995).

Pellicciari et al., "6α-Ethyl-Chenodeoxycholic Acid (6-ECDCA), a Potent and Selective FXR Agonist Endowed with Anticholestatic Activity", *J. Med. Chem.*, 45(17):3569-3572 (2002).

"AGA Technical Review on the Evaluation of Liver Chemistry Tests", Gastroenterology, vol. 123, p. 1367-1384 (2002).

Appendix A (as filed during examination proceedings), 2 pages.

Bramlett et al. "Correlation of Farnesoid X Receptor Coactivator Recruitment and Cholesterol 7a-Hydroxylase Gene Repression by Bile Acids", Molecular Genetics and Metabolism, vol. 71, pp. 609-615 (2000).

Brunt EM. "Nonalcoholic Steatohepatitis", Seminars in liver disease, vol. 24, No. 1, p. 3-20 (2004).

Cipriani et al. "Decoding the role of the nuclear receptor SHP in regulating hepatic" Scientific Reports, vol. 7, 14 pages (2017).

Confirmation that Brunt was publically available in Feb. 2004.

Confirmation that Fernández et al. was published in Jan. 2004.

Curriculum Vitae of Dr. Michele T. Pritchard, 31 pages (2017).

Declaration of Dr. Michele T. Pritchard, 6 pages (2017).

(56) References Cited

OTHER PUBLICATIONS

Dufour et al. "Diagnosis and Monitoring of Hepatic Injury. I. Performance Characteristics of Laboratory Tests", Clinical Chemistry, vol. 46, No. 12, p. 2027-2049 (2000).

Dufour et al. "Diagnosis and Monitoring of Hepatic Injury. II. Recommendations for Use of Laboratory Tests Screening, Diagnosis, and Monitoring", Clinical Chemistry, vol. 46, No. 12, p. 2050-2068 (2000).

Fernandez et al. "Diagnostic and therapeutic approach to cholestatic liver disease", Rev Esp Enferm Dig, vol. 96, No. 1, p. 60-73 (2004).

Fickert et al. "Farnesoid X Receptor Critically Determines the Fibrotic Response in Mice but is Expressed to a Low Extent in Human Hepatic Stellate Cells and Periductal Myofibroblasts", The American Journal of Pathology, vol. 175, No. 6, p. 2392-2405 (2009).

Nueschwander-Tetri, B.A. et al. (2015) Lancet 385(9972): 956-65.

Giannini et al. "Liver enzyme alteration: a guide for clinicians", Canadian Medical Association Journal, vol. 172, No. 3, p. 367-379 (2005).

Gressner et al. "Modern pathogenetic concepts of liver fibrosis suggest stellate cells and TGF-β as major players and therapeutic targets", J. Cell. Mol. Med., vol. 10, No. 1, p. 76-99 (2006).

Heathcote J. "Update on primary biliary cirrhosis", Can J Gastroenterol, vol. 14, No. 1, p. 43-48 (2000).

INT-747 (6-ECDCA) Intercept Pharmaceuticals Pharmacology and Toxicology Information, p. 461-470 (2006).

Jung et al. "Experimental Model of Hepatic Following Repeated Periportal Necrosis Induced by Allylalcohol", Scandinavian Journal of Gastroenterology, vol. 9, p. 969-975 (2002).

Laurin et al. "Ursodeoxycholic Acid or Clofibrate in the Treatment of Non-Alcohol-Induced Steatohepatitis: A Pilot Study", Hepatology, vol. 23, No. 6, p. 1464-1467 (1996).

Li et al. "Inhibition of Endothelin-1-Mediated Contraction of Hepatic Stellate Cells by FXR Ligand", PLoS One, vol. 5, No. 11, e13955, 9 pages (2010).

Lindor et al. "Ursodeoxycholic Acid for Treatment of Nonalcoholic Steatohepatitis: Results of a Randomized Trial", Hepatology, vol. 39, No. 3, p. 770-778 (2004).

Liu et al. "Hepatocarcinogenesis in FXR Mice Mimics Human HCC Progression That Operates through HNF1α Regulation of FXR Expression", Mol. Endocrinol. vol. 26, No. 5, p. 775-785 (2012).

Maeda et al. "Oral Bile Acid Treatment in Two Japanese Patients With Zellweger Syndrome", Journal of Pediatric Gastroenterology and Nutrition, vol. 35, p. 227-230, (2002).

Neuschwander-Tetri et al. "Farnesoid X nuclear receptor ligand obeticholic acid for non-cirrhotic, non-alcoholic steatohepatitis (FLINT): a multicentre, randomised, placebo-controlled trial", The Lancet, vol. 385, No. 956 (2015).

Ratziu et al. "Liver Fibrosis in Overweight Patients", Gastroenterology, vol. 118, p. 1117-1123 (2000).

Setchell et al. "Oral Bile Acid Treatment and the Patient with Zellweger Syndrome", Hepatology, vol. 15, No. 2, p. 198-207 (1992).

Verbeke et al., "FXR agonist obeticholic acid reduces hepatic inflammation and fibrosis in a rat model of toxic cirrhosis", Nature Scientific Reports; vol. 6, p. 33453 (12 pages) (2016).

Vogel et al. "An immortalized rat liver stellate cell line (HSC-T6): a new cell model for the study of retinoid metabolism in vitro", Journal of Lipid Research, vol. 41, p. 882-893 (2000).

Wang et al. "Endogenous Bile Acids Are Ligands for the Nuclear Receptor FXR/BAR", Molecular Cell, vol. 3, p. 543-553 (1999).

Wells R.G. "The Role of Matrix Stiffness in Hepatic Stellate Cell Activation and Liver Fibrosis", Journal of Clinical Gastroenterology, vol. 39, No. 2, p. S158-S161 (2005).

Wikipedia entry about "Alcoholic hepatitis", 3 pages, (2017).

Wildman R. et al. "Advanced human nutrition", p. 321 (4 pages) (2000).

Xu et al. "Bile Acid Receptor Modulators in Metabolic Diseases", Annual Reports in Medicinal Chemistry, vol. 46, p. 69-87 (2011).

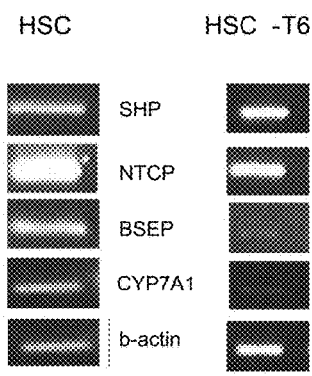
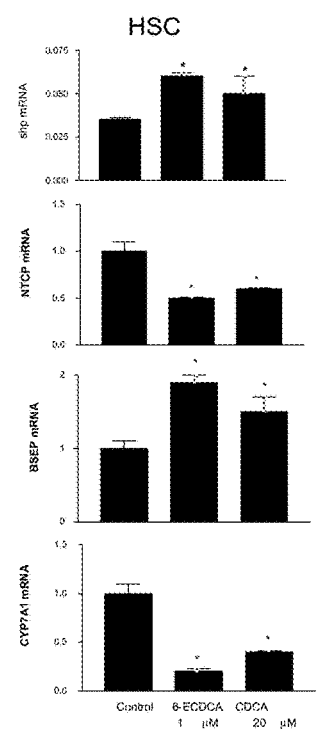
Figure 2A
Figure 2B

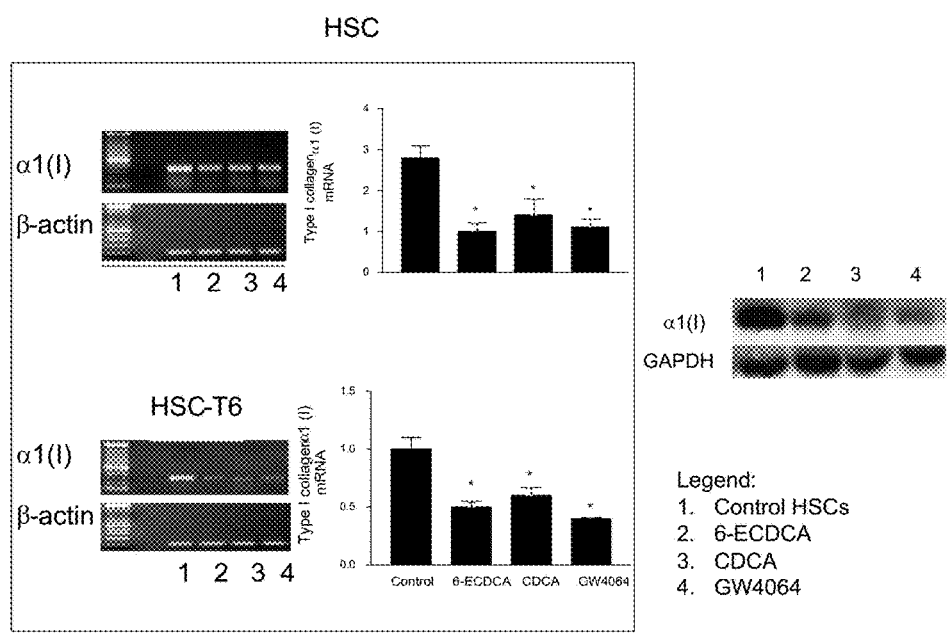
Figure 3A                    Figure 3B

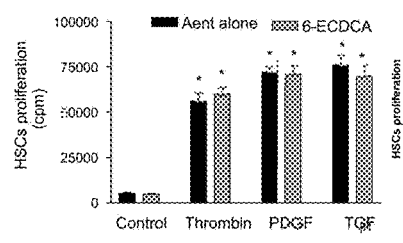
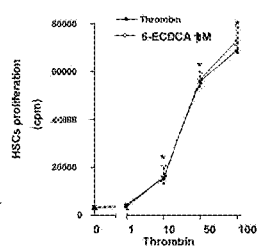
Figure 4A　　　　　　　Figure 4B
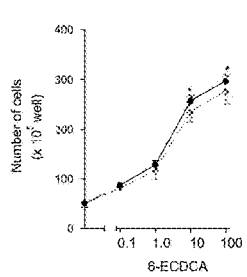
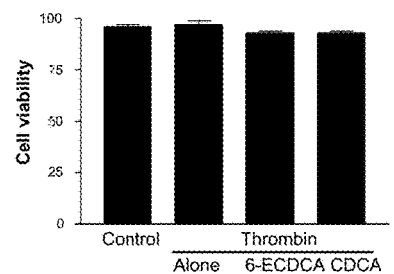
Figure 4C　　　　　　　Figure 4D

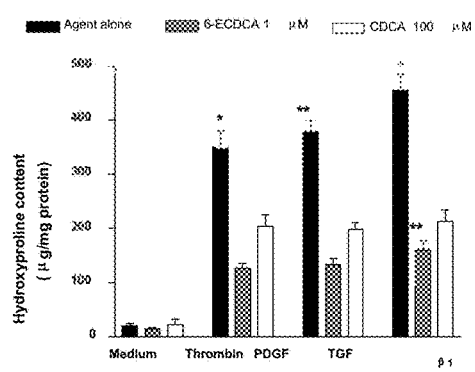
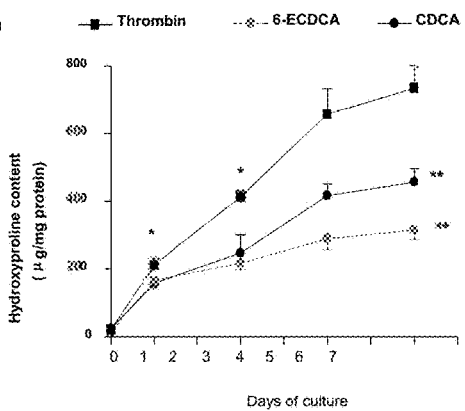
Figure 5A                    Figure 5B

SEQUENCE LISTING

<160> NUMBER OF SEQ ID NOS: 14

<210> SEQ ID NO 1
<211> LENGTH: 17
<212> TYPE: DNA
<213> ORGANISM: Rat

<400> SEQUENCE: 1
cctggagcag ccctcgt                                                  17

<210> SEQ ID NO 2
<211> LENGTH: 22
<212> TYPE: DNA
<213> ORGANISM: Rat

<400> SEQUENCE: 2
aacactgtat gcaaaccgag ga                                            22

<210> SEQ ID NO 3
<211> LENGTH: 23
<212> TYPE: DNA
<213> ORGANISM: Rat

<400> SEQUENCE: 3
tggactcata cagcaaacag aga                                           23

<210> SEQ ID NO 4
<211> LENGTH: 23
<212> TYPE: DNA
<213> ORGANISM: Rat

<400> SEQUENCE: 4
gtctgaaacc ctggaagtct ttt                                           23

<210> SEQ ID NO 5
<211> LENGTH: 19
<212> TYPE: DNA
<213> ORGANISM: Rat

<400> SEQUENCE: 5
tctccaagag gcagggttc                                                19

<210> SEQ ID NO 6
<211> LENGTH: 19
<212> TYPE: DNA
<213> ORGANISM: rat

<400> SEQUENCE: 6
ggttagcttc ggctcatgc                                                19

<210> SEQ ID NO 7
<211> LENGTH: 20
<212> TYPE: DNA
<213> ORGANISM: rat

<400> SEQUENCE: 7
gaagcagagc atgaccttga                                               20

<210> SEQ ID NO 8
<211> LENGTH: 20

```
<212> TYPE: DNA
<213> ORGANISM: rat

<400> SEQUENCE: 8
gacgtgagaa ggtccgagtt                                           20

<210> SEQ ID NO 9
<211> LENGTH: 20
<212> TYPE: DNA
<213> ORGANISM: rat

<400> SEQUENCE: 9
atcttgggct gctcaaactc                                           20

<210> SEQ ID NO 10
<211> LENGTH: 20
<212> TYPE: DNA
<213> ORGANISM: rat

<400> SEQUENCE: 10
gccaccttag ggtagaggaa                                           20

<210> SEQ ID NO 11
<211> LENGTH: 20
<212> TYPE: DNA
<213> ORGANISM: rat

<400> SEQUENCE: 11
ttaatgtcac gcacgatttc                                           20

<210> SEQ ID NO 12
<211> LENGTH: 21
<212> TYPE: DNA
<213> ORGANISM: rat

<400> SEQUENCE: 12
taccactggc attgttgatg g                                         21

<210> SEQ ID NO 13
<211> LENGTH: 20
<212> TYPE: DNA
<213> ORGANISM: rat

<400> SEQUENCE: 13
catgagcacc agccaaccag                                           20

<210> SEQ ID NO 14
<211> LENGTH: 20
<212> TYPE: DNA
<213> ORGANISM: rat

<400> SEQUENCE: 14
ctggaacagg tcacctgagc                                           20
```

TREATMENT OF FIBROSIS USING FXR LIGANDS

RELATED APPLICATIONS

This application claims priority to provisional U.S. patent application No. 60/552,865, filed Mar. 12, 2004, the contents of which are incorporated herein in the entirety.

FIELD OF THE INVENTION

The present invention relates to the prevention, treatment, and/or reversal of fibrosis. In particular, this invention relates to the novel use of ligands specific for farnesoid X receptor (FXR) in patients with fibrotic liver, intestinal, or renal diseases who do not also suffer from a cholestatic condition, in order to inhibit the development and progression of fibrosis in those tissues where FXR is expressed.

BACKGROUND OF THE INVENTION

Fibrosis is characterized by an excessive accumulation of collagen in the extracellular matrix of the involved tissue. It is a long-standing and challenging clinical problem for which no effective treatment is currently available. The production of collagen is a highly regulated physiological process, the disturbance of which may lead to the development of tissue fibrosis. The formation of fibrous tissue is part of the normal beneficial process of healing after injury. In some cases, however, an abnormal accumulation of fibrous material can severely interfere with the normal function of the affected tissue or even cause the complete loss of function of the affected organ.

Liver fibrosis, for instance, represents a major-medical problem with significant morbidity and mortality. In a variety of liver diseases, chronic injury leads to progressive fibrosis that the liver is able to compensate for over as long as 20-30 years; eventually, however, patients begin to experience symptoms and signs of liver failure due to severe fibrosis and cirrhosis. Worldwide chronic viral hepatitis infections, particularly by Hepatitis B and C virus, represent the major cause of liver fibrosis; however, within the United States chronic alcohol consumption has traditionally been the leading cause of hepatic fibrosis and cirrhosis. Currently, with the rapid increase in the prevalence of obesity in the general population, non-alcoholic fatty liver disease (NAFLD) is becoming the most prevalent condition associated with liver fibrosis and may become the leading cause of liver fibrosis associated morbidity and mortality in coming years. Other known causes of liver fibrosis include parasitic infection, autoimmune diseases, iron or copper storage disorders, and biliary obstruction. Liver fibrosis can be classified as a wound healing response to a variety of chronic stimuli that is characterized by an excessive deposition of extracellular matrix proteins, of which type I collagen predominates. This excess deposition of extracellular matrix proteins disrupts the normal architecture of the liver resulting in structural and functional damages to the organ. If left untreated, liver fibrosis can progress to liver cirrhosis ultimately leading to organ failure and death. Many other debilitating and potentially fatal diseases also lead to fibrosis of organs such as the intestine, kidney, heart, and lung.

Because of the pivotal role of collagen production during fibrosis, many studies have focused on the regulation of collagen expression and proliferation of fibroblasts, the major cell type responsible for collagen synthesis. In the liver, the hepatic stellate cell (HSC) is the primary fibrogenic cell type.

A variety of compounds have been identified as anti-fibrosis agents via different mechanisms of action, including the suppression of collagen expression. For example, pantethine (D-bis-(N-pantothenyl-β-aminoethyl)-disulfide) has been reported to be effective for the inhibition of hepatic fibrosis (U.S. Pat. No. 4,937,266); a hydrazine derivative, benzoic hydrazide, has been shown to be a powerful anti-fibrotic agent (U.S. Pat. Nos. 5,374,660 and 5,571,846); the use of angiotensin inhibitors in combination with nitric oxide stimulators to inhibit the progression of fibrosis is disclosed in U.S. Pat. Nos. 5,645,839 and 6,139,847; U.S. Pat. No. 6,005,009 describes methods using certain pyridoxal benzoyl hydrazones or their analogs for inhibiting fibrosis; U.S. Pat. No. 6,117,445 describes the use of $A_1$ adenosine receptor antagonists and/or $P_{2X}$ purinoceptor antagonists for treating or preventing fibrosis and sclerosis. More recently, somatostatin agonists, hepatocyte growth factors (HGFs), chymase inhibitors, and antagonists of IL-13 have been reported to effectively inhibit fibrosis (U.S. Pat. Nos. 6,268,342, 6,303,126, 6,500,835, and 6,664,227).

The farnesoid X receptor (FXR), also known as the bile acid receptor (BAR) and NR1H4, is a member of the nuclear receptor superfamily of ligand-activated transcription factors and forms, with retinoid X receptor (RXR), a heterodimer receptor crucial for bile acid homeostasis (Forman et al., Cell 81: 687-693, 1995; Lu et al., J. Biol. Chem., 17: 17, 2001). FXR is expressed in various tissues including the liver, kidney, intestine, colon, ovary, and adrenal gland (Forman et al., Cell 81: 687-693, 1995).

Containing a conserved DNA-binding domain (DBD) and a C-terminal ligand-binding domain (LBD), FXR binds to and becomes activated by a variety of naturally occurring bile acids, including the primary bile acid chenodeoxycholic acid (CDCA) and its taurine and glycine conjugates (Makishima et al., Science 284: 1362-1365, 1999; Parks et al., Science 284: 1365-1368, 1999; Wang et al., Mol. Cell., 3: 543-553, 1999). Upon activation, the FXR-RXR heterodimer binds the promoter region of target genes and regulates the expression of several genes involved in bile acid homeostasis. For example, the activation of FXR in the liver leads through the direct induction of the nuclear receptor short heterodimer partner (SHP) to the reduced expression of CYP7A, a gene encoding an enzyme catalyzing the rate-limiting step in bile acid synthesis (Schwartz et al., Curr. Opin. Lipidol., 9: 113-119, 1998); whereas the activation of FXR in the intestine leads to increased expression of a bile acid-binding protein (I-BABP), which is involved in the active transport of bile acids in the ileum (Kanda et al., Biochem. J., 330: 261-265, 1998). For a more detailed list of FXR-regulated genes, see, e.g., WO 03/016288, pages 22-23.

Because of the importance of FXR in bile acid homeostasis, FXR-activating ligands have been proposed for use to treat a variety of cholestatic liver diseases and conditions where the normal enterohepatic bile flow is blocked or has otherwise ceased (see, e.g., WO 02/072598 and WO 03/090745).

While not intending to be bound by any particular theory, the present inventor revealed that FXR activation can down-regulate collagen synthesis and resulting fibrosis through a mechanism involving SHP and other FXR target genes. Thus, FXR-activating ligands are effective anti-fibrosis agents in tissues and organs where FXR is present, such as liver, kidney, intestine, etc. The present disclosure provides a new method for preventing, treating and/or reversing fibrosis, based on the surprising discovery of previously unknown properties of FXR-activating ligands.

BRIEF SUMMARY OF THE INVENTION

In one aspect, this invention provides a method for inhibiting fibrosis in a subject not suffering from an underlying cholestatic condition. This method comprises the step of administering to the subject an effective amount of a ligand specific for the farnesoid X receptor (FXR), in order to inhibit fibrosis that might occur in an organ where FXR is expressed. The FXR ligand used in the claimed method is not chenodeoxycholic acid (CDCA) or ursodeoxycholic acid (UDCA); in the alternative, the ligand has an $EC_{50}$ no greater than 5 µM in a cell-free FXR assay or in a cell-based FXR transactivation assay. In a preferred embodiment, the ligand has an $EC_{50}$ no greater than 1 µM.

In some embodiments, the cholestatic condition is defined as having abnormally elevated serum levels of alkaline phosphatase, γ-glutamyl transpeptidase (GGT), and 5' nucleotidase. In one exemplary embodiment, the abnormally elevated serum level is greater than about 125 IU/L for alkaline phosphatase, greater than about 65 IU/L for GGT, and greater than about 17 IU/L for 5' nucleotidase. In other embodiments, the cholestatic condition is defined as presenting with at least one clinical symptom in addition to having abnormally elevated serum levels of alkaline phosphatase, GGT, and 5' nucleotidase. In one exemplary embodiment, the clinical symptom is itching (pruritus).

In some embodiments, the fibrosis to be inhibited by the method of this invention is liver fibrosis, kidney fibrosis, or intestinal fibrosis. In other embodiments, the subject is not suffering from a cholestatic condition such as primary biliary cirrhosis, primary sclerosing cholangitis, drug-induced cholestasis, hereditary cholestasis, or intrahepatic cholestasis of pregnancy. In yet other embodiments, the subject is not suffering from a cholestatic condition associated with a disease or condition such as primary liver and biliary cancer, metastatic cancer, sepsis, chronic total parenteral nutrition, cystic fibrosis, or granulomatous liver disease.

In some embodiments, the FXR ligand is 6ECDCA, tauro-6ECDCA, 6EUDCA, GW4064, 6α-MeCDCA, 6α-PrCDCA, fexaramine, or guggulsterone.

In some embodiments, the fibrosis to be inhibited is liver fibrosis associated with a disease such as hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; α1-antitrypsin deficiency; Zellweger syndrome; tyrosinemia; fructosemia; galactosemia; vascular derangement associated with Budd-Chiari syndrome, veno-occlusive disease, or portal vein thrombosis; or congenital hepatic fibrosis.

In other embodiments, the fibrosis to be inhibited is intestinal fibrosis associated with a disease such as Crohn's disease, ulcerative colitis, post-radiation colitis, or microscopic colitis.

In some further embodiments, the fibrosis to be inhibited is renal fibrosis associated with a disease such as diabetic nephropathy, hypertensive nephrosclerosis, chronic glomerulonephritis, chronic transplant glomerulopathy, chronic interstitial nephritis, or polycystic kidney disease.

In another aspect, this invention provides a kit for inhibiting fibrosis in a subject not suffering from a cholestatic condition. The fibrosis to be inhibited occurs in an organ where farnesoid X receptor (FXR) is expressed. This kit comprises an effective amount of a ligand specific for FXR and an instructional material teaching the indications, dosage, and schedule of administration of the ligand to the patient. The FXR ligand in the claimed kit is not chenodeoxycholic acid (CDCA) or ursodeoxycholic acid (UDCA); in the alternative, the ligand has an $EC_{50}$ no greater than 5 µM in a cell-free FXR assay or in a cell-based FXR transactivation assay. In a preferred embodiment, the ligand has an $EC_{50}$ no greater than 1 µM.

In some embodiments, the kit is used for inhibiting liver fibrosis, kidney fibrosis, or intestinal fibrosis. In other embodiments, the kit comprises an FXR ligand such as 6ECDCA, tauro-6ECDCA, 6EUDCA, GW4064, 6α-MeCDCA, 6α-PrCDCA, fexaramine, or guggulsterone. In yet other embodiments, the FXR in the claimed kit is presented in a pharmaceutical composition suitable for oral or intravenous administration.

BRIEF DESCRIPTION OF THE DRAWINGS

FIG. 1B also demonstrates that the amount of FXR in HSC increases over time during culture and its increase parallels the expression of α-smooth muscle actin (αSMA), a marker of HSCs differentiation into myofibroblast-like cells.

FIG. 2A shows the expression of NTCP, BSEP, CYP7A1, and SHP in HSC.

FIG. 2B shows the expression of these genes regulated by FXR ligands (panel b). The results of quantitative RT-PCR in FIG. 2B illustrates that exposure to 6-ECDCA (a synthetic FXR ligand) and to CDCA (a natural FXR ligand) leads to a 2-fold increase of SHP and BSEP mRNA and a 50-70% reduction of NTCP and CYP7A1 mRNA.

FIG. 3A shows results of RT-PCR and quantitative RT-PCR, indicating that exposure of HSCs to FXR ligands 6-ECDCA (1 µM), CDCA (20 µM), or GW4064 (100 nM) reduces the expression of type I collagen as measure by assessing α1 mRNA expression by methods.

FIG. 3B shows results of Northern blot analysis, which confirm the results shown in FIG. 3B.

FIG. 4A shows a bar graph of the results of HSC proliferation assays, indicating that 6-ECDCA does not prevent HSCs proliferation induced by thrombin, PDGF, or $TGF^{β1}$, as assessed by determining [$^3$H]-thymidine incorporation.

FIG. 4B shows results of HSC proliferation assays, indicating that 6-ECDCA does not prevent HSCs proliferation induced by thrombin, PDGF, or TGFβ1, as assessed by determining [3H]-thymidine incorporation.

FIG. 4C shows results of HSC proliferation assays, indicating that 6-ECDCA does not prevent HSCs proliferation induced by thrombin, PDGF, or TGFβ1, as assessed by cell counting.

FIG. 4D shows that, FXR ligands do not drive HSCs to apoptosis.

FIG. 5A shows FXR ligands-mediated inhibition of collagen α1 release, as measured by determining hydroxyproline concentrations in cell supernatants.

FIG. 5B is a bar graph showing FXR ligands-mediated inhibition of collagen α1 release, as measured by determining hydroxyproline concentrations in cell.

DEFINITIONS

Figure 1A:
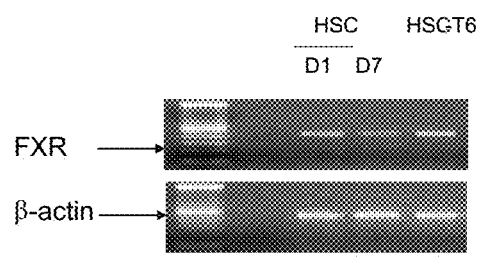
FIG. 1A shows the expression of FXR in the primary cultures of HSCs and HSC-T6, at mRNA level by RT-PCR.

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

The term "inhibiting" or "inhibition," as used herein, refers to any detectable positive effect on the development or progression of a disease or condition. Such a positive effect may include the delay or prevention of the onset of at least one symptom or sign of the disease or condition, alleviation or reversal of the symptom(s) or sign(s), and slowing or prevention of the further worsening of the symptom(s) or sign(s).

As used herein, a "cholestatic condition" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cirrhosis, primary sclerosing cholangitis, sepsis (generalized infection), acute alcoholic hepatitis, drug toxicity, total parenteral nutrition (being fed intravenously), malignancy, cystic fibrosis, and pregnancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ.

Clinical symptoms and signs of a cholestatic condition include: itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what is an abnormally elevated blood level for each of the markers. For example, a patient suffering from a cholestatic condition generally has greater than about 125 IU/L alkaline phosphatase, greater than about 65 IU/L GGT, and greater than about 17 IU/L 5' nucleotidase in the blood. Because of the variability in the level of serum markers, a cholestatic condition may be diagnosed on the basis of abnormal levels of these three markers in addition to at least one of the symptoms mentioned above, such as itching (pruritus).

A "ligand" specific for FXR refers to a natural or synthetic compound that binds to FXR and is thereby capable of specifically stimulating ligand-dependent FXR transcriptional activity differentiated from the baseline level determined in the absence of any ligand. In this application, the term "an FXR ligand" is interchangeable with "an FXR-activating ligand."

The term "effective amount" as used herein refers to an amount of compound (e.g., an FXR-activating ligand) that produces an acute or chronic therapeutic effect upon appropriate dose administration. The effect includes the prevention, correction, inhibition, or reversal of the symptoms, signs and underlying pathology of a disease/condition (e.g., fibrosis of the liver, kidney, or intestine) and related complications to any detectable extent. The exact amount and dosing schedule will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

DETAILED DESCRIPTION OF THE INVENTION

For the first time, ligands specific for the farnesoid X receptor (FXR), particularly those capable of activating FXR at a low concentration, are shown to be effective in treating or preventing fibrosis in tissues or organs such as liver, kidney, and intestine, in patients who are not suffering from a cholestatic condition.

Without being bound to any particular theory, the present inventor discovered that FXR plays an important role in regulating the synthesis of collagen primarily via the actions of SHP that FXR directly regulates in a ligand-dependent fashion. This discovery therefore allows the use of FXR-activating ligands for the effective prevention, treatment, and/or reversal of fibrosis in tissues where FXR is expressed, particularly in patients who are not suffering from any condition for which the use of FXR ligands has been previously suggested, e.g., in cholestatic conditions where the anti-cholestatic therapeutic effect of an FXR ligand may also indirectly inhibit fibrosis.

I. Identification of Patient Population

The present invention relates to the prophylactic and therapeutic use of FXR ligands in patients who: (1) suffer from fibrosis or certain diseases/conditions that are known to lead to fibrosis in a tissue or organ in which FXR is expressed; and (2) do not suffer from a cholestatic condition that may secondarily cause liver fibrosis, where such patients are treated with an FXR ligand to inhibit ongoing liver fibrosis or prevent the development of liver fibrosis. The description below allows for determination if a patient falls within the population suitable for treatment pursuant to the present invention.

A. Expression of FXR in an Organ

One must first determine the status of FXR expression in an organ or a tissue prior to determining whether an FXR ligand may be used to effectively inhibit fibrosis in this organ. The detection of FXR expression can be accomplished at two different levels: nucleic acid level and polypeptide level.

1. FXR Expression at Nucleic Acid Level

The polynucleotide sequence encoding human FXR has been identified by Forman et al. (*Cell* 81: 687-93, 1995) and available as GenBank Accession No. NM_005123. Based on this information, FXR gene expression can be detected at nucleic acid level in a human patient sample. A variety of methods of specific DNA and RNA measurement using nucleic acid hybridization techniques are commonly used (e.g., Sambrook and Russell, *Molecular Cloning, A Laboratory Manual* (3rd ed.) 2001). Some methods involve an electrophoretic separation (e.g., Southern blot for detecting DNA and Northern blot for detecting RNA), but detection of DNA or RNA can be carried out without electrophoresis as well (such as by dot blot, or in situ hybridization if the detection is made within a target tissue). The presence of nucleic acid encoding FXR in the cells of a particular organ can also be detected by polymerase chain reaction (PCR) or PCR-based methods, e.g., real-time PCR and reverse transcription polymerase chain reaction (RT-PCR), using sequence-specific primers.

2. FXR Expression at Protein Level

The expression of FXR in an organ can be confirmed by detecting FXR protein in a tissue sample from this organ. The amino acid sequence of human FXR can be determined based on its coding sequence, e.g., GenBank Accession No. NM_51023, and is set forth in publications such as WO 00/76523. Various immunological assays (such as enzyme-linked immune absorbent assay (ELISA), Western blot, and immunohistochemistry) can be used by those skilled in the art to measure the level of FXR gene product, particularly using polyclonal or monoclonal antibodies that react specifically with the FXR polypeptide, (e.g., Harlow and Lane, *Antibodies, A Laboratory Manual*, Chapter 14, Cold Spring Harbor, 1988; Kohler and Milstein, *Nature,* 256: 495-497, 1975). Such techniques require antibody preparation by selecting antibodies with high specificity against the FXR polypeptide or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.,* 6: 511-519, 1976.

Production of Antibodies against FXR

Methods for producing polyclonal and monoclonal antibodies that react specifically with an immunogen of interest are known to those of skill in the art (see, e.g., Coligan, *Current Protocols in Immunology* Wiley/Greene, NY, 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., human FXR) or an antigenic fragment thereof can be used to immunize suitable animals, e.g., mice, rats, rabbits, goats, horses, or monkeys. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6: 511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity (e.g., specifically recognizing human FXR) or a binding fragment of such antibody by screening a human B cell cDNA library according to the general protocol outlined by Huse et al., supra. The general principles and methods of recombinant polypeptide production discussed above are applicable for antibody production by recombinant methods.

Immunoassays for Detecting FXR Expression

Once antibodies specific for FXR are available, the presence and amount of FXR in a sample, e.g., a small section of tissue, can be measured by a variety of immunoassay methods (such as ELISA or Western blot) providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

(a) Labeling in Immunoassays

Immunoassays often utilize a labeling agent to specifically bind to and label the binding complex formed by the antibody and the target protein (e.g., human FXR). The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g. $^3$H, $^{125}$I, $^{35}$S, $^{14}$C, or $^{32}$P), enzymes (e.g., horse radish peroxidase, alkaline phosphatase, and others commonly used in an ELISA), and colorimetric labels such as colloidal gold or colored glass or plastic (e.g., polystyrene, polypropylene, latex, etc.) beads.

In some cases, the labeling agent is a second antibody bearing a detectable label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111: 1401-1406 (1973); and Akerstrom, et al., *J. Immunol.*, 135: 2589-2542 (1985)).

(b) Immunoassay Formats

Immunoassays for detecting a target protein of interest (e.g., FXR) from samples may be either competitive or noncompetitive. Noncompetitive immunoassays are assays in which the amount of captured target protein is directly measured. In one preferred "sandwich" assay, for example, the antibody specific for the target protein can be bound directly to a solid substrate where the antibody is immobilized. It then captures the target protein in test samples. The antibody/target protein complex □ thus immobilized is then bound by a labeling agent, such as a second or third antibody bearing a label, as described above.

In competitive assays, the amount of target protein in a sample is measured indirectly by measuring the amount of an added (exogenous) target protein displaced (or competed away) from an antibody specific for the target protein by the target protein present in the sample. In a typical example of such an assay, the antibody is immobilized and the exogenous target protein is labeled. Since the amount of the exogenous target protein bound to the antibody is inversely proportional to the concentration of the target protein present in the sample, the target protein level in the sample can thus be determined based on the amount of exogenous target protein bound to the antibody and thus immobilized. See, e.g., Karlson et al., *Lab. Invest.*, 70: 705-710 (1994).

In some cases, western blot (immunoblot) analysis is used to detect and quantify the presence of FXR in the samples. The technique generally comprises separating sample proteins by gel electrophoresis on the basis of molecular weight, transferring the separated proteins to a suitable solid support (such as a nitrocellulose filter, a nylon filter, or a derivatized nylon filter) and incubating the samples with the antibodies that specifically bind the target protein. These antibodies may be directly labeled or alternatively may be subsequently detected using labeled antibodies (e.g., labeled sheep anti-mouse antibodies) that specifically bind to the antibodies against FXR. See, e.g., Pineda et al., *J. Neurotrauma*, 18: 625-634 (2001); Bowler et al., *J. Biol. Chem.*, 277: 16505-16511 (2002).

Various in situ immunochemical staining methods using antibodies against FXR are also useful for demonstrating the presence of FXR in a tissue sample.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.*, 5: 34-41 (1986)).

In addition, functional assays may also be performed for detecting the presence of FXR in a tissue sample. Assays for detecting the biological activity of FXR are generally described in a later section.

B. Diagnosing Fibrosis

Fibrosis is a pathophysiological process in response to tissue injury due to viral or bacterial infection, inflammation, autoimmune disease, trauma, drug toxicity, and so on. During this process, an excess amount of collagen is expressed and fibrous material forms in the extracellular space of the affected tissue. Thus, fibrosis can be generally recognized based on the distinct morphology of fibrous tissue in a biopsy of the organ in which fibrosis is suspected. Other means for detecting the presence of fibrosis or developing fibrosis include computerized axial tomography (CAT or CT) scan, ultrasound, magnetic resonance imaging (MRI), and monitoring the level of one or more serum markers known to be indicative of fibrosis (e.g., various types of collagens).

The precise manner of diagnosing fibrosis also varies depending on the organ where the fibrotic process takes place. For instance, biopsies are generally effective for diagnosing fibrosis of most organs, whereas endoscopy involving a fiber optic instrument (e.g., a sigmoidoscope or a colonoscope) can be a less traumatic alternative to detect fibrosis of certain organs such as the intestine.

1. Biopsy for Detecting Liver Fibrosis

Standard procedures have been established for obtaining biopsy from a given organ. For example, a liver specimen can be obtained during exploratory surgery, but is more often obtained by inserting a biopsy needle through the skin and into the liver. Before this procedure, termed percutaneous liver biopsy, is performed, the person receives a local anesthetic. Ultrasound or CT scans may be used to locate the abnormal area from which the specimen is to be taken.

In transvenous liver biopsy, a catheter is inserted into a neck vein, threaded through the heart, and placed into one of the hepatic veins that drain the liver. The needle of the catheter is then inserted through the wall of the vein into the liver. This procedure is less likely to injure the liver than is percutaneous liver biopsy. It is especially useful in people who bleed easily, which is a complication of severe liver disease.

Upon obtaining a liver biopsy, the sample is examined and given a score to indicate the presence and level of fibrosis in the sample. Most frequently used scoring systems include the METAVIR or modified HAI (ISHAK) scoring system. The Knodell scoring system can also be used for analyzing the liver sample. The criteria used in scoring liver samples are well established and known to those of skilled in the art. For example, the METAVIR system provides five gradings:

F0 indicates the absence of fibrosis; F1 indicates portal fibrosis without septa; F2 indicates portal fibrosis and some septa; F3 indicates septal fibrosis without cirrhosis; and F5 indicates the presence of cirrhosis. See, e.g., Bedossa and Poynard, *Hepatology* 24: 289-293, 1996.

Biopsy is not only useful for the diagnosis of liver fibrosis, it can also aid physicians to assess the effectiveness of fibrosis treatment/prevention methods of the present invention by monitoring the progression of fibrosis using methodologies known in the art. See, e.g., Poynard et al., *Lancet* 349: 825, 1997.

2. Serum Markers for Liver Fibrosis

There are numerous known serum markers whose level can be indicative of the presence and/or severity of liver fibrosis. Blood tests measuring markers, e.g., hyaluronic acid, laminin, undulin (type IV collagen) pro-peptides from types I, II, and IV collagens, lysyl oxidase, prolyl hydroxylase, lysyl hydroxylase, PIIINP, PICP, collagen VI, tenascin, collagen XIV, laminin P1, TIMP-1, MMP-2, $\alpha 2$ macroglobulin, haptoglobin, gamma glutamyl transpeptidase, $\gamma$ globulin, total bilirubin, apolipoprotein A1, etc., according to the established methods can thus be useful for both the diagnosis of fibrosis and monitoring of fibrosis progression in the liver.

3. Other Markers

Additional markers, such as nucleic acid markers, can be used for detecting and/or monitoring fibrosis. For instance, Wnt-4 has recently been indicated in laboratory experiments as a gene that plays an important role in renal fibrosis, where its mRNA expression is significantly increased in the fibrotic tissue in the kidney (see, e.g., Surendran et al., *J Pediatr.* 140: 119-24, 2002). The quantitative detection of gene expression of this type of markers can be useful in the diagnosis and monitoring of fibrosis.

C. Identifying Patients with Elevated Risk of Developing Fibrosis

Because the method of the present invention is also effective for the prevention of the onset of fibrosis or the slowing of its progression after onset, patients with heightened risk of fibrosis fall within the patient population suitable for treatment using the method of the present invention. Such patients are identified based on prior diagnosis of certain diseases and conditions known to lead to fibrosis. The following sections describe the means to diagnose some of these diseases and conditions. There are, however, additional diseases/conditions that are known to elevate a patient's risk of developing fibrosis later in life and that can be readily diagnosed by a physician. The treatment of patients suffering from any of these diseases/conditions with an FXR ligand to prevent, inhibit, or reverse fibrosis is within the contemplation of the present inventor and within the scope of the present invention. Such treatment may be warranted for a short through lifetime course, as is warranted for a given patient with a given disease/condition and as determined by one skilled in the art of treating such patients.

1. Liver Fibrosis

The following are some examples of diseases known to significantly increase a patient's risk of developing liver fibrosis: (i) chronic liver infections (including chronic hepatitis B and hepatitis C viral infection; schistosomiasis and other parasitic liver diseases; post-transplant bacterial, viral and fungal infections); (ii) alcoholic liver disease; (iii) non-alcoholic fatty liver disease (NAFLD) or non-alcoholic steatohepatitis (NASH); (iv) drug and chemical induced liver diseases (including methotrexate, isoniazid, oxyphenistatin, methyldopa, chlorpromazine, tolbutamide, and amiodarone); (v) autoimmune disease (including autoimmune hepatitis, sarcoidosis, and lupoid hepatitis); (vi) storage diseases resulting from inborn errors of metabolism (including Wilson's disease, hemochromatosis, Gaucher's disease, types III, IV, VI, IX and X glycogen storage diseases, $\alpha 1$-antitrypsin deficiency, Zellweger syndrome, tyrosinemia, fructosemia, and galactosemia); (vii) vascular derangement (including Budd-Chiari syndrome, veno-occlusive disease, and portal vein thrombosis); and (viii) congenital hepatic fibrosis.

Hepatitis B

Hepatitis B causes inflammation of the liver due to the infection by hepatitis B virus (HBV, a DNA virus belonging to the family of Hepadnaviridae). An acute HBV infection usually lead to recovery, but rarely can also lead to acute liver failure, and sometimes to chronic infection. The chronic infection can result in a healthy carrier state or progress through fibrosis to cirrhosis and its complications, including liver cancer.

Acute hepatitis B is the initial, rapid onset, short duration illness that results from infection with HBV. About 70% of adults with acute hepatitis B have few or no symptoms, whereas the remaining 30% develop significant symptoms two to four months following exposure to the HBV. The most common symptoms of acute hepatitis B are fatigue, loss of appetite, nausea, vomiting, dark urine, light stools, and abdominal pain over the region of the liver. Jaundice often accompanies these other symptoms.

The diagnosis of chronic hepatitis B can be made, by definition, only after six months from the onset of acute hepatitis B. Most individuals with chronic hepatitis B infection remain asymptomatic for many years, even up to two or three decades. During this time, the patient's liver blood tests usually are at most mildly abnormal and the inflammation and scarring (i.e., fibrosis) of the liver progresses slowly. Occasionally, however, these individuals with otherwise inactive chronic hepatitis B may develop flares (reactivation) of acute symptoms, elevated liver blood tests, and inflammation of the liver. These flares resemble acute hepatitis and can cause more rapid progression of liver fibrosis.

Besides the above-described symptoms, diagnosis of hepatitis B is confirmed by blood test detecting antibodies against HBV.

Hepatitis C

Infection by the hepatitis C virus (HCV, an RNA virus and a member of the Flaviviridae family) is one of the most significant health problems affecting the liver. More than 4 million Americans (1.3% of the U.S. population) and an estimated 170 million individuals in the world (3% worldwide) are infected with HCV. About 85% of individuals initially infected with this virus will become chronically infected, usually for decades. The other 15% of HCV infected individuals simply have an acute infection.

At the beginning of an HCV infection, only about 25% of patients exhibit the characteristic symptoms of acute hepatitis. These symptoms include fatigue, muscular aches, poor appetite, and low-grade fever. Rarely, yellowing of the skin and/or eyes (jaundice) also occurs.

As the hepatitis becomes chronic, most individuals remain asymptomatic and can only be diagnosed through routine blood work when HCV antibodies are detected. In well compensated disease, infected individuals may exhibit no symptoms despite the progressive liver inflammation, necrosis, and fibrosis that is a ubiquitous feature of the chronic infectious process. Other patients may experience chronic or intermittent fatigue and a diminished sense of well-being as a result of advancing disease. On the other hand, fatigue has been described in some individuals with relatively mild disease.

A number of diagnostic tests are currently available for HCV infection. Screening tests are done to determine the presence of antibodies to HCV in the blood. The enzyme immunosorbent assay (EIA) is the conventional, initial screening test to diagnose HCV infection by measuring specific antibodies to HCV antigens. This test, therefore, is referred to as the anti-HCV antibody test. Patients who have elevated liver enzymes (ALT/AST) and/or any of the risk factors for HCV can be diagnosed to have HCV with a greater than 95% certainty when the EIA is positive.

When an individual with low risk of HCV infection is tested positive by EIA, confirmatory testing is conducted using a specialized assay that likewise tests for antibodies against the HCV proteins. This assay is called the Recombinant Immunoblot Assay (RIBA).

Since HCV is an RNA virus, several diagnostic assays are based on the detection of the HCV RNA in a person's blood. These tests are referred to as molecular tests because they examine the virus at the molecular level. The two most common systems for measuring HCV RNA are the reverse transcription polymerase chain reaction (RT-PCR) assay and the branched chain DNA (bDNA) assay. Recently, a third type of assay, called transcription-mediated amplification (TMA), has been become available.

Alcoholic Liver Disease

Alocholic liver disease (ALD) is a chronic liver disease caused by excessive consumption of alcohol. The symptoms of ALD are usually non-specific, and do not necessarily indicate the severity of the underlying liver damage. General ALD symptoms include fatigue, nausea and vomiting, diarrhea, or abdominal pains. Many patients, even with advanced ALD marked by progressive liver fibrosis and toxicity, may have no symptoms and their condition is only diagnosed by liver blood tests. Only in the more advanced stages of decompensated ALD (severe alcoholic hepatitis or cirrhosis) will the sufferer present with more specific liver-related symptoms such as jaundice, ascites, hematemesis, or encephalopathy.

The diagnosis of ALD is established based on a history of alcohol abuse, blood tests showing the presence and severity of liver damage. Ultrasound scan of the liver can help assess the severity of disease and exclude other conditions with similar symptoms. Liver biopsy is the most reliable means to determine the present and stage of ALD.

Non-Alcoholic Fatty Liver Disease

Non-alcoholic fatty liver disease (NAFLD) refers to a wide spectrum of liver diseases ranging from simple fatty liver (steatosis), to non-alcoholic steatohepatitis (NASH), to cirrhosis. All of the stages of NAFLD have in common the accumulation of fat in the hepatocytes. In NASH, the fat accumulation is associated with varying degrees of inflammation (hepatitis) and scarring (fibrosis) of the liver. NAFLD and NASH occur in individuals who do not consume excessive amounts of alcohol. Yet, in many respects, the histological picture of an NAFLD biopsy is similar to what can be seen in liver disease caused by alcohol abuse. NAFLD and NASH are considered the primary fatty liver diseases. The secondary fatty liver diseases include those that occur in other types of liver disease. Thus, alcoholic liver disease (ALD) is the most frequent secondary fatty liver disease. Secondary fatty liver can also occur in chronic viral hepatitis C (HCV), chronic viral hepatitis B (HBV), chronic autoimmune hepatitis (AIH), and Wilson's disease.

The symptoms of NAFLD and NASH are identical. They are usually not dramatic and tend to be non-specific (as can also be observed in other diseases). The symptoms are minimal in most patients, who may, however, experience occasional, vague right upper-quadrant abdominal pain. This pain characteristically is dull and aching, without a predictable pattern of occurrence. It is not an intense, sudden, and severe pain, as might occur with, for example, gallstones. The abdominal pain in NAFLD and NASH is thought to be due to the stretching of the liver covering (capsule) when the liver enlarges and/or when there is inflammation in the liver. In contrast to ALD, hepatitis B, or hepatitis C, symptoms of severe, acute liver failure (e.g., jaundice, intense fatigue, loss of appetite, nausea, vomiting, and confusion) are not observed in NAFLD or NASH. Obesity and related conditions (e.g., diabetes, hypertension) are frequent seen among those suffering from NAFLD or NASH, and the classic signs of insulin resistance often dominate the physical exam in NAFLD and NASH. Acanthosis nigricans, a dark pigmentation of the skin of the armpits and neck, can be a sign of insulin resistance and is frequently seen in children with NASH. When the liver is palpated, it usually feels normal. However, when very large amounts of fat accumulate in the liver, it can be become quite large with a soft, rounded edge that can be easily felt by the doctor.

In addition to the symptoms described above, a diagnosis of NAFLD or NASH is made based on the following criteria: clinical and/or biochemical signs of insulin resistance; chronically elevated ALT; signs of fatty liver on ultrasound; exclusion of other causes of elevated ALT and fatty liver. Only a liver biopsy, however, can establish a definite diagnosis and determine the severity of NAFLD or NASH.

Parasitic Liver Diseases

Various parasitic diseases are known to damage the liver and lead to fibrosis or even cirrhosis. Clonorchiasis, for instance, is an infection by the liver fluke *Clonorchis sinensis*. Patients initially infected with this parasite usually have no symptoms until the worm load reaches more than 500. Common symptoms are chills, diarrhea, fever, lower abdominal pain, jaundice, and swelling of the liver. To diagnose the disease, a medical history should be taken including questions on diet, travel, regions where previously resided. A physical examination should include gentle palpation of the liver. Further testing includes endoscopy and examination of stool sample for eggs.

*O. tenuicollis* (*O. felineus*) and *O. viverrini* are two other parasites that are closely related to *Clonorchis sinensis* and can lead to permanent liver damage. The diagnostic methods are similar to that described above. Close comparison of the morphology of the eggs and adult worms is necessary to distinguish the infections by these parasites.

Schistosomiasis is another parasitic disease of liver, gastrointestinal tract, and bladder caused by schistosomes, trematode worms that parasitize people who come into contact with contaminated water.

There are three main species of these trematode worms (flukes)—*Schistosoma haematobium*, *S. japonicum*, and *S. mansoni*—that cause disease in humans. Within days after infection, a patient may develop a rash or itchy skin. Fever, chills, cough, and muscle aches can begin within 1-2 months of infection, even though most people have no symptoms at the early phase of infection. Eggs of the parasites travel to the liver or pass into the intestine or bladder. Rarely, eggs are found in the brain or spinal cord and can cause seizures, paralysis, or spinal cord inflammation. For people who are repeatedly infected for many years, the parasite can damage the liver, intestines, lungs, and bladder.

The diagnosis of schistosomasis involves examination of a patient's stool or urine samples for the eggs and/or the adult parasite. A blood test has been developed to detect antibodies against this parasite. Medical history reflecting possible exposure to contaminated water is also helpful for making a proper diagnosis.

Autoimmune Hepatitis

Autoimmune hepatitis, also known as lupoid hepatitis, involves inflammation of the liver caused by immune cells that mistake the liver's normal cells for a foreign tissue or pathogen. A person with autoimmune hepatitis has autoantibodies circulating in the bloodstream that cause the immune system to attack the liver. This disease is associated with other autoimmune diseases, including: thyroiditis, type 1 diabetes, ulcerative colitis, hemolytic anemia, and proliferative glomerulonephritis.

Symptoms of autoimmune hepatitis may include dark urine, loss of appetite, fatigue, general discomfort, uneasiness, or ill feeling (malaise), abdominal distention, generalized itching, pale or clay-colored stools, nausea, and vomiting.

Diagnosis can be made based on several criteria such as liver biopsy showing chronic hepatitis and fibrosis, abnormal liver function tests, as well as tests associated with autoimmune hepatitis, e.g., positive antinuclear antibodies, positive anti-smooth muscle antibody, positive anti-liver kidney microsomal antibody, positive anti-mitochondrial antibody, elevated sedimentation rate, elevated serum IgG.

Sarcoidosis

Another autoimmune disease that affects the liver is sarcoidosis. Sarcoidosis is a disease that causes small lumps, or granulomas, due to chronic inflammation to develop in a great range of body tissues. Sarcoidosis can appear in almost any body organ, but most often starts in the lungs or lymph nodes. It also affects the eyes, liver and skin; and less often the spleen, bones, joints, skeletal muscles, heart and central nervous system (e.g., brain and spinal cord). In the majority of cases, the granulomas clear up with or without treatment. In cases where the granulomas do not heal and disappear, the tissues tend to remain inflamed and become fibrotic.

Neonatal Liver Diseases

Neonatal liver diseases refer to severe liver disorders that occur in newborns in the neonatal period (i.e., the first 60 days of life). The possible causes of these disorders may include viral infection, hereditary metabolic diseases, neoplasia, and vascular problems. The infants affected frequently have jaundice, do not gain weight and grow normally, and have enlarged liver and spleen. The infants cannot absorb vitamins for proper growth.

In addition to the above symptoms, the diagnosis of neonatal liver diseases is aided by liver biopsy, especially in the cases where the condition is not caused by viral infection.

Wilson's Disease

Wilson's Disease is an inherited autosomal recessive disorder in which too much copper accumulates in the body. Although the accumulation of copper begins at birth, symptoms of the disorder appear later in life, between the ages of 6 and 40. A diagnostic feature of Wilson's Disease is what is called a Kayser-Fleischer ring, a deep copper-colored ring around the edge of the cornea. It represents copper deposits in the eye.

The most significant clinical consequence for about 40 percent of patients with Wilson's Disease is liver disease. In other patients, the first symptoms are neurological or psychiatric or both, and include tremor, rigidity, drooling, difficulty with speech, abrupt personality change, grossly inappropriate behavior, and inexplicable deterioration of performance at school or work, neurosis or psychosis.

Wilson's Disease can also be diagnosed by genetic testing to identify both copies of mutated gene, which has been localized to chromosome 13 between 13q14.3-q21.1.

Hemochromatosis

Hemochromatosis is an inherited disorder of excessive body accumulation of iron. It is common among the white population, affecting approximately 1 in 400 individuals of European ancestry. Hemochromatosis patients are believed to absorb from their diet excessive amounts of iron, which becomes accumulated over time in the liver, bone marrow, pancreas, skin, and testicles.

Patients with early hemochromatosis have no symptoms, and the disease may be discovered when elevated iron blood levels are noted by routine blood testing. In males, symptoms may not appear until 40-50 years of age. Iron deposits in the skin cause darkening of the skin. Since females lose iron through menstrual blood loss, they develop organ damage from iron accumulation 15-20 years later than men on average.

Iron deposits in the pituitary gland and testicles cause shrinkage of the testicles and impotence. Iron deposits in the pancreas cause a decrease in insulin production resulting in diabetes mellitus. Iron deposits in the heart muscle can cause heart failure as well as abnormal heart rhythms. Iron accumulation in the liver causes scarring of the liver (fibrosis and cirrhosis) and an increased risk of developing liver cancer.

Initial screening for hemochromatosis involves tests for levels of blood iron and ferritin, the latter is a blood protein that serves as an indicator of the amount of iron stored in the body. Blood iron and ferritin levels are high in patients with. Since ferritin can also be elevated in certain infections, such as viral hepatitis and other inflammations in the body, ferritin increase alone is not sufficient to accurately diagnose hemochromatosis.

The most accurate test for hemochromatosis is measuring the iron content of liver tissue obtained by a biopsy. A biopsy involves the removal of a sample of liver tissue for analysis and is usually performed with a needle under local anesthesia. After numbing the skin and the underlying tissues, the doctor inserts a needle into the liver through the right lower rib cage, sometimes under ultrasound guidance. The tissue obtained by the needle is studied under a microscope for liver damage or cirrhosis. The amount of iron in the liver is usually significantly elevated in hemochromatosis.

Finally, genetic testing can effectively confirm a diagnosis of hemochromatosis. The gene for hereditary hemochromatosis, HFE, was identified in 1996 and can be identified in blood testing of 90 percent of patients with northern European ancestry.

Glycogen Storage Diseases

Glycogen storage diseases (GSD), also known as glycogenoses, are genetically linked metabolic disorders that involve the enzymes regulating glycogen metabolism and are characterized by deposition of an abnormal type of quantity of glycogen in the tissues. GSDs often manifest the symptoms early in a patient's infancy or childhood. In some cases, however, the conditions may go undetected until adulthood or even old age. Varying by type, there are four major symptoms that typically lead a doctor to suspect GSDs: low blood sugar, enlarged liver, retarded growth, and an abnormal blood biochemistry profile. A definitive diagnosis is obtained by biopsy of the affected organ or organs, where the biopsy sample is tested for its glycogen content and assayed for enzyme activity. There are DNA-based techniques for diagnosing some GSDs from more easily available samples, such as blood or skin. These DNA techniques can also be used for prenatal testing.

In certain types of GSDs, disruption of glycogen metabolism often leads to the accumulation of abnormal metabolic by-products, which can damage organs such as the liver and the kidneys. Among all GSDs, types III, IV, VI, IX, and X are the most relevant to the onset of liver fibrosis.

Type III glycogen storage disease (Cori's disease) is characterized by the absence of debranching enzyme, amylo-1,6-glucosidase which causes the accumulation of a polysaccharide of the limit dextrin type. The structure of glycogen stored in the liver and muscle is abnormal and the amount is markedly increased. Most noticeable is the short outer branch of the glycogen, thus only a small portion of this abnormal glycogen is functionally active as an accessible source of glucose. Symptoms of this disorder include enlargement of the liver, hypoglycemia, ketosis, hyperuricemia, hyperlipemia, etc. In youths affected by this disease, growth is impaired, puberty is often delayed, and bones may be weakened by osteoporosis. Blood platelets are also affected and frequent nosebleeds and easy bruising are common. Primary symptoms improve with age, but after age 20-30, liver tumors, chronic renal disease, and gout may appear. The diagnosis of this condition is based on the above symptoms and confirmed by examining of the glycogen structure.

Type IV glycogen storage disease (Andersen's disease) is characterized by the absence of branching enzyme ($\alpha$-1,4 to $\alpha$-1,6), with the result that the glycogen constructed in type IV GSD has very long outer branches and is insoluble. As the abnormal glycogen accumulates in the cells, cell death leads to organ damage. Infants born with GSD IV appear normal at birth, but are diagnosed with enlarged livers and failure to thrive within their first year. Infants who survive beyond their first birthday develop cirrhosis of the liver by age 3-5 and die as a result of chronic liver failure. The diagnosis of this disease is aided by the detection of the characteristic abnormal glycogen structure.

Type VI glycogen storage disease (Hers' disease) is caused by liver phosphorylase deficiency, which blocks the first step of glycogenolysis. In contrast to most other GSDs, which involve autosomal mutations, type VI GSD is linked to the X chromosome. In this disease, phosphorylase deficiency results in increased amount of glycogen in the liver. Symptoms include enlargement of the liver, hypoglycemia, ketosis, hyperuricemia, hyperlipemia, etc. Low blood sugar is one of the key symptoms. Mildly retarded growth can occur in affected youths.

Type IX glycogen storage disease is caused by liver glycogen phosphorylase kinase (PhK) deficiency and, symptom-wise, is very similar to type VI GSD. The main differences are that the symptoms may not be as severe and may also include exercise-related problems in the muscles, such as pain and cramps. The symptoms abate after puberty with proper treatment. Most cases of GSD IX are linked to the X chromosome and therefore affect males. Enzymatic testing and measuring glycogen content provides a definitive diagnosis.

An enzyme that activates glycogen phosphorylase to stimulate glycogen breakdown in various tissues, PhK is a tetrameric enzyme made up of four different subunits ($\alpha\beta\gamma\delta$) that are responsible for various subtypes of GSD IX, that differ both in tissue affected (liver/muscle/RBC/Cardiac tissue) and in mode of inheritance. The genes for $\alpha$, $\beta$, and $\gamma$ subunits have been cloned and mapped to X chromosome ($\alpha$), chromosome 16q12 ($\beta$), and chromosome 7p12 ($\gamma$).

The most common form of PhK deficiency is the X-linked form, and it mainly affects the liver. Clinically patients with this form of PhK deficiency present in infancy with hepatomegaly, mild hypoglycemia, growth retardation, hyperlipidemia, hyperketosis, and delayed motor development. The symptoms improve with age, and adult patients have normal stature and normal liver.

The autosomal recessive form of PhK deficiency affects both liver and muscle depending on whether mutation has occurred in the $\alpha$ or $\beta$ subunit of the enzyme. Symptoms could range from mild myopathy with muscle cramping to severe myopathic form.

Type X glycogen storage disease is an autosomal recessive disease caused by a deficiency of a cyclic adenosine monophosphate (AMP)-dependent phosphoglycerate mutase and presents symptoms similar to GSDs VI and IX. The gene involved in this condition has been mapped to chromosome 7p12-p13.

$\alpha$1-Antitrypsin Deficiency $\alpha$1-antitrypsin deficiency is a hereditary disease in which a lower-than-normal level of $\alpha$1-antitrypsin is present in the lungs. $\alpha$1-antitrypsin is a protein that is made in the liver and then released into the bloodstream. In normal lungs, $\alpha$1-antitrypsin protects the lungs from the harmful effects of neutrophil elastase. In a patient suffering from $\alpha$1-antitrypsin deficiency, damage to lung tissues by neutrophil elastase may lead to emphysema and breathing difficulty. The most noticeable symptom of this disorder is the shortness of breath during daily activities. Liver diseases associated with this disease include those with early onset, such as hepatitis or neonatal jaundice, or those with late onset, such as cirrhosis and primary cancer of the liver (Hepatoma).

$\alpha$1-antitrypsin deficiency can be diagnosed based on symptoms such as shortness of breath and a chronic cough. Blood test for $\alpha$1-antitrypsin level and pulmonary function test can also aid the diagnosis. Since this disease is caused by an autosomal recessive mutation, the most definitive diagnosis is based on results of genetic testing.

Gaucher's Disease

Gaucher's disease is caused by a genetic defect in an enzyme glucocerebrosidase. This enzyme helps the body break down the chemical glucocerebroside. The defective enzyme in patients with Gaucher's disease leads to the accumulation of glucocerebroside in the spleen, liver, and lymph nodes. Gaucher's disease is most common in Ashkenazi Jews (those of European origin), however, variants have been described in all ethnic groups. Depending on the precise type of the disease, affected patients may have varying degrees of symptoms. The most frequent early sign of Gaucher's disease is enlargement of the spleen. There can be associated fatigue, anemia, and a low count of platelets. Severe bone involvement can lead to pain and collapse (aceptic necrosis) of the bone of the hips, shoulders, and spine. Poor lung and brain function, and even seizures, can occur.

The diagnosis of Gaucher's disease is confirmed by a special test in which the activity of $\beta$-glucocerbrosidase of fibroblasts activity is measured. Patients with Gaucher's disease have less than 15% of the normal level of glucocerebrosidase. Because of the genetic nature of the disease, diagnosis based on gene testing is also possible.

Zellweger Syndrome

Zellweger syndrome is a genetic disorder, also called the cerebrohepatorenal syndrome, characterized by the reduction or absence of peroxisomes in the cells of the liver, kidneys, and brain. Zellweger syndrome is one of a group of disorders called the leukodystrophies, all of which affect the myelin sheath, the fatty covering which acts as an insulator on nerve fibers in the brain. The most common features of Zellweger syndrome include an enlarged liver, high levels of iron and copper in the blood, and vision disturbances. Some affected infants may show prenatal growth failure. Symptoms at birth may include lack of muscle tone and an inability to move. Other symptoms may include unusual facial characteristics, mental retardation, seizures, and an inability to suck and/or swallow. Jaundice and gastrointestinal bleeding may also occur.

This disease is caused by mutations in any of several different genes involved in peroxisome formation. These genes lie on at least two different chromosome locations including chromosome 2 (region 2p15) and chromosome 7 (region 7q21-q22). Thus, its diagnosis can be confirmed by genetic testing.

Tyrosinemia

Hereditary tyrosinemia is a genetic inborn error of metabolism associated with severe liver disease in infancy. The disease is inherited in an autosomal recessive fashion. The clinical features of the disease tend to fall into two categories: in the acute form of the disease, abnormalities appear in the first month of life. Babies may show poor weight gain, enlarged liver and spleen, distended abdomen, swelling of the legs and increased tendency to bleeding, particularly nose bleeds. Jaundice may or may not be prominent. In a more chronic form of tyrosinemia, enlargement of the liver and spleen are prominent, the abdomen is distended with fluid, weight gain may be poor, and vomiting and diarrhea occur frequently. Affected patients usually develop cirrhosis and its complications. In older patients, there is an increases risk of liver cancer.

In diagnosing this disease, liver tests are often used. Low serum albumin and clotting factors are frequently found. The liver enzymes transaminases may be mildly to moderately elevated, but the bilirubin is increased to a variable extent. Because of the biochemical defect, abnormal products may be measured in the urine which confirm diagnosis. These are parahydroxy phenylactic acid and parahydroxy phenylpyruvic acid. In addition, succinylacetone and succinylacetoacetate are found in the urine. There may be hypoglycemia and evidence of loss of certain substances in the urine including sugar, protein, and amino acids. The basic biochemical defect is an abnormality in a key enzyme in the metabolism of an essential amino acid, phenylalanine. The enzyme is fumarylacetoacetate hydrolase (FAH), which is markedly reduced in affected patients. Prenatal diagnosis is possible and can be performed by measuring succinylacetone in the amniotic fluid or fumarylacetoacetate hydrolase (FAH) in amniotic fluid cells.

Fructosemia

Fructosemia, also known as fructose intolerance or fructose aldolase B-deficiency, is a metabolic disease caused by the absence of an enzyme, 1-phosphofructaldolase (i.e., fructose aldolase B). Hereditary fructose intolerance is inherited as an autosomal recessive disease. It may be as common as 1 in 20,000 in some European countries. In fructose-intolerant people, ingestion of fructose (fruit sugar) and sucrose (cane or beet sugar, table sugar) produces complicated chemical changes that cannot be corrected because of the absence of the enzyme 1-phosphofructaldolase. Ingestion of fructose causes profound hypoglycemia and progressive liver damage. The diagnosis of this condition is based on the fructose intolerant symptoms, test results that measure the level of fructose aldolase B, and genetic analysis to identify mutation(s) in the gene.

Galactosemia

Galactosemia is a rare hereditary disease leading not only to cirrhosis in infants, but more seriously, to early devastating illness if not diagnosed quickly. This disease is caused by elevated levels of galactose in the blood resulting from a deficiency of the liver enzyme, GALT (galactose-1-phosphate uridyl transferase), required for its metabolism. Galactosemia is inherited as an autosomal recessive trait. There are two forms of the disease, GALT deficiency (classic galactosemia) and galactose kinase deficiency. Of the two, the GALT deficiency is the most severe. The GALT gene is in chromosome 9p13.

People with galactosemia are unable to metabolize the simple sugar galactose. If an infant with galactosemia is given milk, galactose builds up in the infants system causing damage to the liver, brain, kidneys and eyes. Individuals with galactosemis cannot tolerate any form of milk (human or otherwise) or any other galactose-containing food. Exposure to milk products will result in liver damage, mental retardation, cataract formation, and kidney failure. Typically, a newborn infant with galactosemia, upon being fed milk, will develop jaundice, vomiting, lethargy, irritability, and convulsions. The liver is enlarged and the blood sugar may be low. Continued feeding of milk products to the infant leads to cirrhosis of the liver, cataract formation in the eye resulting in partial blindness, and mental retardation.

The symptoms of galactosemia include jaundice, vomiting, poor feeding, poor weight gain, lethargy, irritability, convulsions, and opacities in the lenses of the eyes. The signs detected include hepatomegaly, hypoglycemia, aminoaciduria, cirrhosis, ascites, cataracts, and mental retardation.

The diagnosis is usually based on the demonstration of a lack of activity of the enzyme GALT in erythrocytes. Prenatal diagnosis is also feasible by direct measurement of the enzyme. DNA-based testing is also possible for diagnosing the condition.

Chronic Inflammatory Condition

Chronic inflammatory hepatic condition is a progressive liver disease and can lead to fibrosis or death if complete liver failure occurs. Cause of this condition may be bacterial or viral infection, exposure to toxic agents, or in some cases, unknown.

Clinical signs of this disease can range from mild to severe. Typical symptoms may include fatigue, weight loss, nausea, vomiting, increased urination and defecation, fluid collecting in the abdomen (ascites), jaundice, blood in the stool, and abnormal neurological behavior. A definitive diagnosis of chronic inflammatory hepatic disease is made by examination of a biopsy specimen.

Vascular Derangement

Vascular disorders may also contribute to the heightened risk of liver fibrosis. The most frequent abnormality of circulation to affect the liver is congestive heart failure, which leads to reduced outflow of blood from the liver. Other causes of hepatic congestion include constrictive pericarditis, obstruction of the inferior vena cava and hepatic veins (Budd-Chiari syndrome), occlusion of the small hepatic veins (veno-occlusive disease), and portal vein thrombosis. Increased resistance to hepatic venous outflow results in congestive hepatomegaly, dilation of hepatic venules and sinusoids, and hypoxia. The hypoxia in turn leads to hepatocyte damage with possible fibrosis and cirrhosis.

Drug Toxicity

Toxins such as alcohol, drugs, or poisons can cause hepatitis directly (by damaging liver tissue) or indirectly (by reducing defenses or stimulating an autoimmune response); both can lead to liver fibrosis.

Alcohol is primarily metabolized by the liver, producing various metabolites that can cause liver damage. The risk of hepatic toxicity increases if more than 40 grams of alcohol, or about four drinks, are consumed per day.

Numerous medications can damage the liver, ranging from mild, asymptomatic alteration in liver chemistries to hepatic failure and death. Liver toxicity may or may not be dose-related. Dilantin (an anti-convulsant), methotrexate (a drug used to treat various neoplastic diseases, psoriasis and rheumatoid arthritis), chlorpromazine (an anti-psychotic drug), and isoniazid (an anti-tuberculosis agent) are examples of drugs that can cause "viral-like" hepatitis.

Both environmental and industrial toxins can cause a wide variety of changes in the liver. Hepatic damage is not necessarily dose-dependent and can range from mild, asymptomatic inflammation to fulminant failure or progressive fibrosis and cirrhosis.

Patients with risk of developing liver fibrosis due to their exposure to drugs or toxins are generally identified by review of their medical history and continued monitoring of their liver function.

Congenital Hepatic Fibrosis

Congenital hepatic fibrosis (CHF) is a rare hereditary disorder characterized by periportal fibrosis with irregularly shaped proliferating bile ducts, intrahepatic portal hypertension, and esophageal varices. CHF is associated with an impairment of renal functions, usually caused by an autosomal recessive polycystic kidney disease (ARPKD). The disease is inherited in an autosomal recessive fashion, but sporadic cases do occur. The typical liver abnormalities include hepatomegaly, portal hypertension, and hepatic fibrosis. Many patients with CHF also show bleeding from the gastrointestinal tract (e.g., from stomach and intestines). Diagnosis of CHF is made based on these symptoms, especially the association with ARPKD. Genetic testing is also a possible means for diagnosing the condition.

2. Intestinal Fibrosis

Several diseases are known to increase a patient's risk of developing intestinal fibrosis, including: Crohn's disease, ulcerative colitis, post-radiation colitis, and microscopic colitis.

Crohn's Disease

Crohn's disease is a chronic inflammatory disease of the intestines. It primarily causes ulcerations (breaks in the lining) of the small and large intestines, but can affect the digestive system anywhere from the mouth to the anus. It also is called granulomatous enteritis or colitis, regional enteritis, ileitis, or terminal ileitis. The cause of Crohn's disease is not yet understood. It has traditionally been classified as an autoimmune disease and some scientists now suspect that infection by certain bacteria, such as strains of mycobacterium, may be the cause of this disease.

Common symptoms of Crohn's disease include abdominal pain, diarrhea, and weight loss. Less common symptoms include poor appetite, fever, night sweats, rectal pain, and rectal bleeding. The symptoms of Crohn's disease are dependent on the location, the extent, and the severity of the inflammation. The different subtypes of Crohn's disease and their symptoms are:

(1) Crohn's colitis is inflammation that is confined to the colon. Abdominal pain and bloody diarrhea are the common symptoms. Anal fistulae and peri-rectal abscesses also can occur.

(2) Crohn's enteritis refers to inflammation confined to the small intestine (the first part, called the jejunum or the second part, called the ileum). Involvement of the ileum alone is referred to as Crohn's ileitis. Abdominal pain and diarrhea are the common symptoms. Obstruction of the small intestine also can occur.

(3) Crohn's terminal ileitis is inflammation that affects only the very end of the small intestine (terminal ileum), the part of the small intestine closest to the colon. Abdominal pain and diarrhea are the common symptoms. Small intestinal obstruction also can occur.

(4) Crohn's entero-colitis and ileo-colitis are terms to describe inflammation that involve both the small intestine and the colon. Bloody diarrhea and abdominal pain are the common symptoms. Small intestinal obstruction also can occur.

Crohn's terminal ileitis and ileo-colitis are the most common types of Crohn's disease. Up to one third of patients with Crohn's disease may have one or more of the following conditions involving the anal area:

(1) Swelling of the tissue of the anal sphincter, the muscle at the end of the colon that controls defecation.

(2) Development of ulcers and fissures (long ulcers) within the anal sphincter. These ulcers and fissures can cause bleeding and pain with defecation.

(3) Development of anal fistulae (abnormal tunnels) between the anus or rectum and the skin surrounding the anus). Mucous and pus may drain from the openings of the fistulae on the skin.

(4) Development of peri-rectal abscesses (collections of pus in the anal and rectal area). Peri-rectal abscesses can cause fever, pain and tenderness around the anus.

The diagnosis of Crohn's disease is suspected in patients with fever, abdominal pain and tenderness, diarrhea with or without bleeding, and anal diseases. Laboratory blood tests may show elevated white cell counts and sedimentation rates, both of which suggest infection or inflammation. Other blood tests may show low red blood cell counts (anemia), low blood proteins, and low body minerals, reflecting loss of these elements due to chronic diarrhea.

Barium x-ray studies can be used to define the distribution, nature, and severity of the disease. Barium is a chalky material that is visible by x-ray and appears white on x-ray films. When barium is ingested orally (Upper GI Series), it fills the intestine and pictures (x-rays) can be taken of the stomach and the small intestines. When barium is administered through the rectum (Barium Enema), pictures of the colon and the terminal ileum can be obtained. Barium x-rays can show ulcerations, narrowing, and, sometimes, fistulae of the bowel.

Direct visualization of the rectum and the large intestine can be accomplished with flexible viewing tubes (colonoscopes). Colonoscopy is more accurate than barium x-rays in detecting small ulcers or small areas of inflammation of the colon and terminal ileum. Colonoscopy also allows for small tissue samples (biopsies) to be taken and sent for examination under the microscope to confirm the diagnosis of Crohn's disease. Colonoscopy also is more accurate than barium x-rays in assessing the degree (activity) of inflammation.

Computerized Axial Tomography (CAT or CT) scanning is a computerized x-ray technique that allows imaging of the entire abdomen and pelvis. It can be especially helpful in detecting abscesses.

Most recently, video capsule endoscopy has been added to the list of diagnostic tests for diagnosing Crohn's disease. For video capsule endoscopy, a capsule containing a minature video camera is swallowed. As the capsule travels through the small intestine, it sends video images of the lining of the small intestine to a receiver carried on a belt at the waist. The images are downloaded and then reviewed on a computer. The value of video capsule endoscopy is that it can identify the early, mild abnormalities of Crohn's disease. Video capsule endoscopy may be particularly useful when there is a strong suspicion of Crohn's disease but the barium x-rays are normal. (Barium x-rays are not as good at identifying early, mild Crohn's disease.)

Ulcerative Colitis

Ulcerative colitis is another chronic inflammatory condition that is closely related to Crohn's disease but usually involves only the rectum, or rectum and sigmoid colon at the distal end of the colon. These are called ulcerative proctitis and procto-sigmoiditis, respectively. Collectively, Crohn's disease and ulcerative colitis are frequently referred to as inflammatory bowel disease (IBD).

Common symptoms of ulcerative colitis include rectal bleeding and diarrhea, but there is a wide range of symptoms among patients with this disease. Variability of symptoms reflects differences in the extent of disease (i.e., the amount of the colon and rectum that are inflamed) and the intensity of inflammation. Generally, patients with inflammation confined to the rectum and a short segment of the colon adjacent to the rectum have milder symptoms and a better prognosis than patients with more widespread inflammation of the colon. The different types of ulcerative colitis are classified according to the location and the extent of inflammation:

(1) Ulcerative proctitis refers to inflammation that is limited to the rectum. In many patients with ulcerative proctitis, mild intermittent rectal bleeding may be the only symptom. Other patients with more severe rectal inflammation may, in addition, experience rectal pain, urgency (sudden feeling of having to defecate and a need to rush to the bathroom for fear of soiling), and tenesmus (ineffective, painful urge to move one's bowels).

(2) Proctosigmoiditis involves inflammation of the rectum and the sigmoid colon (a short segment of the colon contiguous to the rectum). Symptoms of proctosigmoiditis, like that of proctitis, include rectal bleeding, urgency, and tenesmus. Some patients with proctosigmoiditis also develop bloody diarrhea and cramps.

(3) Left-sided colitis involves inflammation that starts at the rectum and extends up the left colon (sigmoid colon and the descending colon). Symptoms of left-sided colitis include bloody diarrhea, abdominal cramps, weight loss, and left-sided abdominal pain.

(4) Pancolitis or universal colitis refers to inflammation affecting the entire colon (right colon, left colon, transverse colon and the rectum). Symptoms of pancolitis include bloody diarrhea, abdominal pain and cramps, weight loss, fatigue, fever, and night sweats. Some patients with pancolitis have low-grade inflammation and mild symptoms that respond readily to medications. Generally, however, patients with pancolitis suffer more severe disease and are more difficult to treat than those with more limited forms of ulcerative colitis.

(5) Fulminant colitis is a rare but severe form of pancolitis. Patients with fulminant colitis are extremely ill with dehydration, severe abdominal pain, protracted diarrhea with bleeding, and even shock. They are at risk of developing toxic megacolon (marked dilatation of the colon due to severe inflammation) and colon rupture (perforation). Patients with fulminant colitis and toxic megacolon are treated in the hospital with potent intravenous medications. Unless they respond to treatment promptly, surgical removal of the diseased colon is necessary to prevent colon rupture.

The diagnosis of ulcerative colitis is suggested by the symptoms of abdominal pain, rectal bleeding, and diarrhea. As the first step, stool specimens are collected for analysis to exclude infection and parasites, since these conditions can cause colitis that mimics ulcerative colitis. Blood tests may then be conducted and show anemia and an elevated white blood cell count or sedimentation rate (commonly referred to as SED rate). An elevated white blood cell count and SED rate both reflect ongoing inflammation in the colon. Confirmation of ulcerative colitis requires a test to visualize the large intestine. Flexible tubes inserted through the rectum (sigmoidoscopes and colonoscopes) permit direct visualization of the inside of the colon to establish the diagnosis and to measure the extent of the colitis. Small tissue samples (i.e., biopsies) can be obtained during the procedure to determine the severity of the colitis. Knowledge of the extent and severity of the colitis is important in choosing among treatment options. A barium enema x-ray may also indicate the diagnosis of ulcerative colitis. During a barium enema, a chalky substance is administered into the rectum and injected into the colon. Barium is radio-paque and can outline the colon on x-ray pictures. A barium enema is less accurate and useful than direct visualization techniques in the diagnosis of ulcerative colitis.

Post-Radiation Colitis

Post-radiation colitis is a type of persistent colon irritation that occurs in patients who have been previously exposed to a significant amount of irradiation, such as those who have received radiotherapy for treating cancers. Although the general symptoms are similar to those of non-radiation related irritated colon conditions, such as pain and chronic diarrhea, patients suffering from post-radiation colitis are easily identified based on their medical history.

Microscopic Colitis

Microscopic colitis (MC) encompasses the two morphologically distinct entities of collagenous colitis (CC) and lymphocytic colitis (LC). Patients with MC generally present with chronic diarrhea, which can be associated with cramping and bloating. Endoscopic and radiological examinations are usually normal. Histological assessment reveals inflammation consisting predominantly of lymphocytic infiltration, and a thickened subepithelial collagen band is diagnostic of CC. Both LC and CC can be associated with autoimmune diseases such as celiac disease, diabetes, arthritis, and thyroiditis, yet the precise mechanisms involved in the pathogenesis remain unclear.

3. Renal Fibrosis

A variety of kidney diseases and conditions are known to increase a patient's likelihood of developing renal fibrosis, eventually leading to end-stage renal disease and the need for dialysis and transplant. These diseases and conditions include: diabetic nephropathy, hypertensive nephrosclerosis, chronic glomerulonephritis, chronic transplant glomerulopathy, chronic interstitial nephritis, polycystic kidney disease, and other less common diseases affecting the kidney.

Diabetic Nephropathy

Diabetic nephropathy is a kidney disease associated with long-standing diabetes. Also known as Kimmelstiel-Wilson disease (or syndrome), it affects the network of tiny blood vessels (the microvasculature) in the glomerulus, a key structure in the kidney that is composed of capillary blood vessels and is critically necessary for the filtration of the blood.

The symptoms of this disease include excessive filtration of protein into the urine (proteinuria), frothy urine (signifying protein in urine), high blood pressure (hypertension), leg swelling (worse after walking/standing), itching, nausea/vomiting, unexplained weight loss, fatigue/lethargy, increased need to urinate at night, and requiring less pills or insulin to control diabetes.

Diabetic nephropathy generally causes progressively impaired kidney function. In its severe form, this disease can lead to kidney failure and end-stage renal disease, and a patient may require chronic kidney dialysis or a kidney transplant. Diabetic nephropathy is also referred to as intercapillary glomerulonephritis.

Hypertensive Nephrosclerosis

Hypertensive nephrosclerosis is the hardening (sclerosis) of the kidney in connection with hypertension. The kidney plays an important role in regulating blood pressure. Kidney diseases may affect the function of the kidneys and disrupt such regulation, resulting in elevated blood pressure. On the other hand, kidney damages may result from hypertension for a prolonged period, as high blood pressure can affect the cardiovascular system by causing the blood vessels to narrow and thicken.

At its early stage, hypertensive nephrosclerosis may not display any significant symptoms for a long time. When present, common symptoms include: high blood pressure, headache, neck discomfort, fatigue, nausea or vomiting, and protein in urine (proteinuria).

Chronic Glomerulonephritis

Glomerulonephritis is an inflammatory condition that affects predominantly the glomeruli, the filtering heads of the nephrons in the kidney. Chronic glomerulonephritis usually leads to end-stage kidney disease.

The general symptoms of glomerulonephritis include blood or protein in urine, frothy urine (usually indicative of protein in urine), dark or pink-colored urine, leg swelling, systemic diseases such as diabetes or autoimmune diseases with systemic manifestations, e.g., unexplained weight loss, arthritis, or skin rash.

There are a number of different conditions that may cause glomerulonephritis or result from glomerulonephritis. Some of these conditions are discussed below. One example of a glomerulonephritis-related condition is IgA nephropathy, a kidney disease where Ig A deposits inside the glomeruli within the kidney. The IgA deposits prevent this filtering process, leading to the symptoms of blood and protein in the urine and swelling in the hands and feet. This disease causes glomerular inflammation that ultimately results in the impairment or even the complete loss of kidney function.

Autoimmune diseases can also give rise to glomerulonephritis. One such example is lupus nephritis (or glomerulonephritis secondary to lupus). In other cases, infections by bacteria (e.g., Streptococcus) or viruses (e.g., HIV or HBV), particularly in children under the age of ten, can cause post-infection glomerulonephritis.

Glomerulonephritis also relates to focal segmental glomerulosclerosis (FSGS), an illness that occurs when scar tissue forms in some of the glomeruli of the kidney. The term "focal" means that some of the glomeruli become scarred, while others remain normal. The term "segmental" means that only part of an individual glomerulus is damaged. Symptoms of FSGS include foamy urine, swelling of the body (i.e., generalized edema, from retained fluids), weight gain, and poor appetite.

A diagnosis can be made based on: a urinalysis, which shows protein, with or without small amounts of blood; a renal biopsy, which shows evidence of scarring; and an immunofluorescence microscopy test, which shows deposits of IgM.

There are two types of Membranoproliferative glomerulonephritis, which are kidney disorders with similar symptoms that result in disrupted or decreased kidney function, caused by inflammation and changes in the microscopic structure of kidney cells. Symptoms include: blood in the urine, dark urine, cloudy urine, decrease in urine volume, swelling of any part of the body, changes in mental status (e.g., decreased alertness, decreased concentration). A physical examination will reveal these symptoms to a varying degree. A diagnosis is aided by urinalysis and confirmed by kidney biopsies.

Rapidly progressive glomerulonephritis is a form of kidney disease that causes damage to the internal structures of the kidneys and rapid loss of function, with crescent-shaped abnormalities showing on a biopsy of the kidney. Common symptoms include: edema, dark or smoke-colored urine, blood in the urine, decreased urine volume, fever, muscle aches, joint aches, shortness of breath, cough, general ill-feeling, abdominal pain, loss of appetite, diarrhea, and the like. To diagnose this condition, a physical examination combined with blood tests and urinalysis can reveal many of the above symptoms, as well as increased BUN and creatinine, decreased creatinine clearance, and/or the presence of anti-glomerular basement membrane antibodies and anti-neutrophil cytoplasmic antibodies (ANCAs). A kidney biopsy confirms crescentic glomerulonephritis.

Scleroderma is an autoimmune disease of the connective tissue, also called systemic sclerosis. This condition is characterized by the fibrosis in the skin and organs of the body. The diagnosis of scleroderma is based on the finding of the clinical features of the illnesses. Nearly all patients with scleroderma have blood tests that suggest autoimmunity, antinuclear antibodies (ANAs). A particular antibody, the anticentromere antibody, is found almost exclusively in the limited, or CREST, form of scleroderma. Anti-Scl 70 antibody (antitopoisomerase I antibody) is most often seen in patients with the diffuse form of scleroderma.

Vasculitis is a general term for a group of uncommon diseases that feature the inflammation of the blood vessels, leading to the damages to the walls of various blood vessels. Laboratory testing of blood or body fluids in a patient with active vasculitis generally indicates inflammation in the body. Depending on the degree of organ involvement, a variety of organ function tests may be abnormal and thus indicative of the condition. The diagnosis of vasculitis is ultimately established after a biopsy of involved tissue (e.g., kidney) demonstrates the pattern of blood vessel inflammation. Depending upon the situation, an alternative to biopsy can be an x-ray test of the blood vessels, e.g., an angiogram.

Wegener's granulomatosis (WG) is a rare disease that affects many different organs including the respiratory system (sinuses, nose, windpipe, and the lungs) and the kidneys. One of the main features of the disease is an inflammation of the blood vessels (or vasculitis). The inflammation narrows the blood vessels and reduces the blood flow to the affected organs, subsequently damages affected tissues and organs.

The precise cause of WG remains unknown but is thought to relate to an autoimmune condition. In fact, auto-antibodies are often detected in some WG patients. One of the most common symptoms of WG is a chronic runny nose and other cold-like symptoms that do not respond to standard treatment. The cold symptoms gradually worsen and could lead to sinusitis (inflammation of the sinuses), middle ear infection (otitis media), cough, coughing of blood, and inflammation of the lung (pleuritis and pneumonia). Other symptoms include fever, fatigue, loss of appetite, weight loss, joint pain, night sweats, change in urine color, and weakness. Kidney disease is the most serious development of WG.

The blood tests of WG patients often show anemia (low red cell count) and high white blood cell counts. If the kidneys are involved, red blood cells are seen in the urine when viewed under a microscope. Also, blood tests aimed at measuring kidney function may show abnormalities. Chest X-rays are used to determine if the lungs are involved. Kidney biopsy and CT scans of sinuses or lungs are also important tools used in diagnosing WG.

A specific type of antibody called anti-neutrophil cytoplasmic antibody (ANCA) is seen in the blood of about 90% of the patients with WG. The ANCA is a type of self-antibodies against an individual's own white blood cells (i.e., the neutrophils). These anti-neutrophil cytoplasmic antibodies are also found in other inflammatory conditions and diseases (such as HIV infection). The ANCA test is useful for confirming a diagnosis of WG, but cannot be used by itself to make a diagnosis.

Polyarteritis nodosa (PAN) is a rare autoimmune disease characterized by spontaneous inflammation of the arteries of the body. The most commonly involved organs include intestines and kidneys. Impaired function or pain in any of these organs can be a symptom. Poor blood supply to the bowels can cause abdominal pain and bleeding. Fatigue, weight loss, and fever are also often observed in patients. The cause of PAN is unclear, though it has been reported following HBV infection.

The diagnosis of PAN is supported by tests that indicate inflammation including elevation of blood sedimentation rate and c-reactive protein. The white blood cell count and platelet count can be elevated, while the red blood count is decreased (anemia). Some patients may be positive for the HBV tests. Urine testing can show the presence of protein and red blood cells in the urine. In some cases, abnormalities can be observed in nerve function tests. The diagnosis is confirmed by a biopsy or an angiogram of involved tissue, which reveals the inflamed blood vessels.

In addition, Goodpasture syndrome is an autoimmune disease characterized by a combination of lung and kidney disease—specifically, pulmonary hemorrhage (bleeding in the lungs) and glomerulonephritis (inflammation of the glomerulus)—due to severe inflammation in the basement membranes of the alveolus of the lung and the glomerulus in the kidney with the formation of antibodies to components of the basement membrane at both sites. Clinical symptoms include cough with bloody sputum, bloody urine, decreased urine output, fatigue, hypertension, swelling (edema), and unexplained weight loss. The syndrome has also been named anti-glomerular basement membrane antibody disease.

Chronic Transplant Glomerulopathy

Chronic transplant glomerulopathy refers to a variety of conditions that occur in patients who have received a kidney transplant and have the characteristic changes in kidney structure including mesangial matrix expansion, mesangial proliferation, basement membrane thickening with double contours, and peripheral mesangial interposition, sometimes accompanied by focal segmental sclerosis. These changes are usually associated with marked proteinuria, often in the nephrotic range. Diagnosis of these conditions is made based on review of medical history (whether a patient is a transplant receipient), urinalysis, and kidney biopsy.

Chronic Interstitial Nephritis

Interstitial nephritis is a type of nephritis due to disorders of the connective tissue within the kidney, severe allergic reactions, exposure to toxic substances, transplant rejection, urinary blockage, or other factors, resulting in inflammation of the space between the renal tubules and may include inflammation of the tubules. Symptoms of interstitial nephritis may include fever, pain in the kidney area, increased or decreased urine output, fever, mental status changes (ranging from drowsiness to confusion to coma), nausea or vomiting, rash, swelling of the body, weight gain due to fluid retention, and blood or protein in the urine.

An examination of a patient suffering from interstitial nephritis may reveal edema or fluid overload, or signs of volume depletion, with abnormal sounds heard when listening with a stethoscope to the heart or lungs. The blood pressure commonly is high. A urinalysis often shows small amounts of protein and sometimes red blood cells, renal tubular cells, and other abnormalities. WBCs and WBC casts in the urine (particularly eosinophils) are often seen. CBC may demonstrate eosinophilia (higher than normal eosinophil count). Urine specific gravity and osmolality show there is a failure to concentrate urine even when water intake is restricted. Urine pH may show a failure to acidify urine appropriately. Arterial blood gases and blood chemistry may show metabolic acidosis. BUN and creatinine levels are used to assess level of kidney functioning. RBC—urine shows increased red blood cells indicating kidney disease. Finally, a kidney biopsy can confirm the diagnosis of interstitial nephritis and is used to evaluate the extent of damage to the kidney.

Polycystic Kidney Disease

Polycystic kidney disease (PKD) is a disorder that is characterized by the growth of numerous cysts in the kidneys. The cysts are filled with fluid. PKD cysts can replace much of the mass of the kidneys, thereby reducing kidney function and leading to kidney failure. When PKD causes kidneys to fail, which usually happens only after many years, the patient requires dialysis or kidney transplantation. About one-half of people with the primary form of PKD progress to kidney failure or end-stage renal disease (ESRD).

PKD can cause cysts in the liver and problems in other organs, such as the heart and blood vessels in the brain. These complications help doctors distinguish PKD from the usually harmless "simple" cysts that often form in the kidneys in later years of life.

There are two major inherited forms of PKD and a non-inherited form. Autosomal dominant PKD is the most common, inherited form. Symptoms usually develop between the ages of 30 and 40, but they can begin as early in childhood. About 90 percent of all PKD cases are autosomal dominant PKD. The most common symptoms are pain in the back and the sides (between the ribs and hips), and headaches. The dull pain can be temporary or persistent, mild or severe. People with autosomal dominant PKD also can experience the following problems: urinary tract infections; hematuria (blood in the urine); liver and pancreatic cysts; abnormal heart valves; high blood pressure; kidney stones; aneurysms (bulges in the walls of blood vessels) in the brain; and diverticulosis (small sacs on the colon).

To diagnose autosomal dominant PKD, a doctor typically observes three or more kidney cysts using ultrasound imaging. The diagnosis is strengthened by a family history of autosomal dominant PKD and the presence of cysts in other organs.

In most cases of autosomal dominant PKD, the person's physical condition appears normal for many years, even decades, so the disease can go unnoticed. Physical checkups and blood and urine tests may not lead to diagnosis. Once cysts have formed, however, diagnosis is possible with imaging technology. Ultrasound is used most often. Since ultrasound imaging employs no injected dyes or radiation and is safe for all patients, including pregnant women. It can also detect cysts in the kidneys of a fetus.

More powerful imaging methods such as CAT scan and MRI also can detect cysts. The advancement in molecular technology has also made DNA testing a possibility to confirm a diagnosis of autosomal dominant PKD before cysts develop.

Autosomal recessive PKD is a second inherited form of the disease. It is relatively rare. Autosomal recessive PKD is caused by a genetic defect that is different from the one that causes autosomal dominant PKD. Parents who do not have the disease can have a child with the disease if both parents carry the abnormal gene and both pass the gene to their baby. The chance of this happening (when both parents carry the abnormal gene) is one in four. If only one parent carries the abnormal gene, the baby cannot get the disease.

The symptoms of autosomal recessive PKD can begin in the earliest months of life, even in the womb, so it is often called "infantile PKD." Children born with autosomal recessive PKD usually develop kidney failure within a few years. The severity of the disease varies. Babies with the worst cases die hours or days after birth. Children with an infantile version may have sufficient renal function for normal activities for a few years. People with the juvenile version may live into their teens and twenties and usually suffer liver problems as well.

Children with autosomal recessive PKD display symptoms including high blood pressure, urinary tract infections, and frequent urination. The disease usually affects the liver, spleen, and pancreas, and causes low blood-cell counts, varicose veins, and hemorrhoids. Because kidney function is crucial for early physical development, children with autosomal recessive PKD are usually smaller than average size.

In diagnosing this disease, ultrasound imaging of the fetus or newborn baby can reveal cysts in the kidneys, but does not distinguish between the cysts of auto-somal recessive and autosomal dominant PKD. An ultrasound examination of relatives' kidneys can be helpful in making the correct diagnosis. For example, a parent or grandparent with autosomal dominant PKD cysts could help confirm the diagnosis of autosomal dominant PKD in a fetus or child. It is extremely rare, although not impossible, for a person with autosomal recessive PKD to become a parent. Because autosomal recessive PKD tends to scar the liver, ultrasound imaging of the liver also aids in the diagnosis.

Similar to the diagnosis of autosomal dominant PKD, autosomal recessive PKD can also be definitively diagnosed based on DNA analysis.

Acquired cystic kidney disease (ACKD) is a non-inherited form of PKD and tends to occur in later years of life. ACKD often develops in association with long-term kidney problems (e.g., kidney damage and scarring), especially in patients who have kidney failure and who have been on dialysis for a long time. About 90 percent of people on dialysis for 5 years develop ACKD. Patients with ACKD can have any underlying kidney disease, such as glomerulonephritis or the kidney disease caused by diabetes.

The cysts of ACKD may bleed. Thus, the first noticeable symptom of ACKD is blood in the urine, or hematuria. Diagnosis of ACKD is confirmed using ultrasound, CAT scan, or an MRI of the kidneys. In addition, kidney tumors, including kidney (renal) cancer, can also develop in people with ACKD. Although renal cancer is rare, it occurs at least twice as often in ACKD patients as in the general population.

II. The Exclusion of Cholestatic Conditions

A. Cholestatic Conditions

Although various cholestatic conditions are likely to lead to liver fibrosis, the present invention does not encompass the treatment/prevention of liver fibrosis in a patient who is already suffering from a cholestatic condition, such as primary biliary cirrhosis, primary sclerosing cholangitis, drug-induced cholestasis, hereditary cholestasis, and intrahepatic cholestasis of pregnancy, cholestasis associated with total parenteral nutrition, sepsis, and cystic fibrosis. The following describes how to exclude patients with these cholestatic conditions when practicing the present invention.

B. Diagnosis of Cholestatic Conditions

The typical symptoms of a cholestatic condition include itching (pruritus), fatigue, jaundiced skin or eyes, inability to digest certain foods, nausea, vomiting, pale stools, dark urine, and right upper quadrant abdominal pain. Organ failure may occur in cases of sepsis (but not from cholestasis itself), and rash or fever may result in some cases of drug-induced cholestasis.

The diagnosis of a cholestatic condition is generally based on the detection of elevated levels of conjugated bilirubin, alkaline phosphatase, γ-glutamyltranspeptidase (GGT), 5' nucleotidase, bile acids, and cholesterol in a patient's blood. For each of the above-named conditions, specific diagnostic criteria may apply.

Primary biliary cirrhosis (PBC) is a chronic disease characterized by slow, progressive inflammation and destruction of the small bile ducts within the liver. The inflammation and destruction interfere with the excretion of bile, cause scarring, and eventually lead to cirrhosis. In the early stages of PBC, the main problem is the build up of substances (like bile acids, cholesterol) in the blood, which are normally excreted into the bile. Many PBC patients have no symptoms of disease and are diagnosed by finding an abnormality on routine liver blood tests. Itching and fatigue are common symptoms. Other signs include jaundice, cholesterol deposits in the skin, fluid accumulation in the ankles and abdomen, and darkening of the skin. Several other disorders are often associated with PBC. The most common is impaired functioning of the tear and salivary glands, causing dry eyes or mouth. Arthritis and thyroid problems may also be present. Renal stones and gallstones may develop. Bone softening and fragility leading to fractures can occur in late stages of the disease.

PBC diagnosis is based on several indications: the patient may have symptoms (such as itching) suggesting bile duct damage; laboratory tests, such as the alkaline phosphatase activity test, may confirm the diagnosis. The test for anti-mitochondrial antibodies (AMA) is particularly useful as it is positive in nearly all PBC patients. Infrequently, the bile ducts are X-rayed to rule out possibilities of other causes of biliary tract disease, such as obstruction. A liver biopsy is useful in confirming the diagnosis and in giving information on the severity and extent of liver damage.

The criteria for a definitive diagnosis of PBC have been established to identify all patients with classic PBC and exclude any patient with a questionable diagnosis. A definitive diagnosis of PBC is made in a patient who has all three of the following: cholestatic liver tests (alkaline phosphatase and GGT elevated more than ALT and AST); AMA positive at a titer of greater than or equal to 1:40; and positive reading of a diagnostic or compatible liver biopsy.

In a patient suffering from primary sclerosing cholangitis (PSC), the bile ducts inside and outside the liver become inflamed and scarred. As the scarring increases, the ducts become blocked, which leads to the buildup of bile in the liver and damages liver cells. Various causes of PSC have been speculated, including bacterial or viral infection or abnormalities of the immune system.

The main symptoms of PSC are itching, fatigue, and jaundice. An infection in the bile ducts can cause chills and fever. PSC is diagnosed through cholangiography, which involves injecting dye into the bile ducts and taking an X ray image. Cholangiography can be performed as an endoscopic procedure (endoscopic retrograde cholangiopancreatography, ERCP), through radiology or surgery, or with magnetic resonance imaging (MRI).

Drug-induced cholestasis refers to blockage of the bile flow from the liver due to certain medication. Many drugs can cause this type of cholestasis. Some more common culprits include: gold salts, nitrofurantoin, anabolic steroids, oral contraceptives, chlorpromazine, prochlorperazine, sulindac, cimetidine, erythromycin, tobutamide, imipramine, ampicillin, and other penicillin-based antibiotics. Other medications can also unexpectedly cause cholestasis in some individuals. Symptoms of drug-induced cholestasis are similar to other cholestatic conditions, namely, itching, jaundiced skin or eyes, very dark urine, very pale stools, fever or rash from drug sensitivity, right upper quadrant abdominal pain, and nausea/vomiting. A diagnosis of drug-induced cholestasis is made based on blood tests revealing elevated bilirubin and alkaline phosphatase levels in addition to a careful review of medical history.

Hereditary cholestasis is an inherited form of cholestatic condition, an autosomal recessive disease. With many symptoms similar to those of the non-hereditary type of cholestasis, this condition is diagnosed and distinguished from the non-hereditary type based on the early onset of the symptoms and family medical history. Genetic testing is the most reliable method for identifying patients with this condition. For instance, ATP8B1 (FIC1) and ABCB11 (BSEP) have been identified as two genes involved in hereditary cholestasis (see, e.g., van Mil et al., *Semin Liver Dis.* 21: 535-44, 2001; Chen et al., *J Pediatr.* 140: 119-24, 2002).

Intrahepatic cholestasis of pregnancy (ICP) is a cholestatic condition seen in pregnant women. Women ICP may show symptoms such as anorexia, fatigue, greasy stools, dark urine, and epigastric discomfort. Urinary tract infections are more common in women with ICP than unaffected pregnant women. Finally, a deficiency of vitamin K can develop in women who have a prolonged course of ICP. The diagnosis of ICP is based on blood tests showing elevated levels of bile acids and certain liver enzymes (e.g., alkaline phosphatase, GGT, 5' nucleotidase). The presence of itching without a primary rash also helps to confirm the diagnosis. A liver biopsy or ultrasound is rarely needed to establish the diagnosis.

Cholestasis associated with total parenteral nutrition is a type of cholestasis that occurs in patients who receive 100% of their nutrition parenterally. Although the clinical features may be similar to other cholestatic conditions, these patients are easy to identify as they are being given liquid nutrition through a catheter intravenously.

Potentially a life-threatening condition, sepsis is also referred to as a "blood stream infection." This condition reflects the body's response to an infection and features the presence of infectious organisms (such as bacterium, virus, fungus, yeast, parasite, etc.) or their toxins in the blood or in other tissue of the body. Sepsis may be associated with clinical symptoms of systemic illness, such as fever, chills, malaise, low blood pressure, and reduced mental alertness. Diagnosis of sepsis is based on blood cultures to detect the presence of bacteria or yeasts, which may have spread from another site in the body.

Cystic Fibrosis (CF), caused by a genetic defect inherited in an autosomal recessive fashion, is a chronic, progressive, and frequently fatal disease of the body's mucus glands. The clinical features of this disease include: chronic infections of the lungs, emphysema, progressive respiratory insufficiency, gastrointestinal problems (including pancreas and liver), pancreatic insufficiency (with no secretion of trypsin and other digestive enzymes into the intestine), intestinal obstruction at birth, continuing deficiency of pancreatic enzymes, biliary tract obstruction, constriction of the common bile duct, cirrhosis of the liver, recurrent episodes of pain in the right lower part of the abdomen, adenocarcinoma of the ileum, heart problems such as cor pulmonale, and reproductive problems such as male infertility. Laboratory tests are necessary for diagnosing CF. A CF patient often shows positive sweat test results, lack of trypsin in the stool (and high level of trypsin in blood serum). The gene implicated in CF has been identified, thus DNA testing is the most reliable diagnostic tool for this condition.

III. FXR Ligands

A. Assays for Identifying FXR Ligands

Several assay systems have been established for identifying FXR ligands, particularly those with high potency to activate FXR. For example, a candidate compound can be tested in a cell-free co-regulator recruitment assay to determine if the compound is an FXR-activating ligand and its efficacy. Briefly, this system utilizes the binding between FXR and a co-regulator protein or peptide. Co-regulators are nuclear proteins known to be recruited to FXR upon FXR's binding to its ligand (e.g., SRC1). The ligand-dependent recruitment of a co-regulator protein or peptide to FXR is measured by various methods such as fluorescence resonance energy transfer (FRET), fluorescence polarization or luminescent proximity assays. Either a human FXR or rat FXR may be used for this purpose. For a detailed description of this assay system, see, e.g., Maloney et al., *J. Med. Chem.*, 43: 2971-2974, 2000; Pellicciari et al., *J. Med. Chem.*, 45: 3569-3572, 2002; Cui et al., *J. Bio. Chem.*, 277: 25963-25969, 2002; and Jones et al., *Methods Enzymol.*, 364: 53-71, 2003.

Alternatively, candidate compounds can be tested for their binding potency to FXR in cell-free assays such as gel filtration or scintillation proximity assays where radioligands are used, see, e.g., Jones et al., *Methods Enzymol.*, 364: 53-71, 2003.

Another assay system useful for testing a compound for its FXR ligand properties is a whole cell model (e.g., in hepatic stellate cells) involving a reporter gene (such as luciferase or β-galactosidase) controlled by a transcription regulatory element responsive to a ligand activated FXR. Either human or rat FXR can be used in the assay. The level of reporter activity indicates a test compound's effectiveness as an FXR activating ligand. For a detailed description of such a reporter gene-based screening system, see, e.g., Goodwin et al., *Mol. Cell.*, 6: 517-526, 2000; Cui et al., *J. Bio. Chem.*, 277: 25963-25969, 2002.

In either of the two classes of assay systems described above, the potency of a particular FXR ligand is measured by its $EC_{50}$ (i.e., the concentration of a ligand necessary to produce 50% of the maximum value of a measured effect) demonstrated during the assay. The FXR ligands suitable for use in the present invention are those with an $EC_{50}$ no greater than 5 µM, preferably no greater than 2 µM, more preferably no greater than 1.5 µM, and most preferably no greater than 1 μM, as determined in a cell-free FXR assay or a cell-based transactivation assay using a human or rat FXR according to the methods described in the references named above.

In addition, there are established methods for the screening of a ligand specific for FXR and not for other nuclear receptors, particularly RXR. For example, WO 00/76523 describes an assay system in which the recombinant RXR is mutated by a single point substitution ($RXR_{D322P}$) to eliminate the RXR ligand-binding site, such that the use of FXR-$RXR_{D322P}$ heterodimer permits unambiguous identification of compounds that are capable of modulating FXR activity.

Compounds of similar or dissimilar chemical structures have demonstrated their ability to specifically bind FXR. For instance, WO00/40965, WO00/76523, WO03/015771, WO03/015777, WO03/016280, WO03/016288, WO03/030612, and WO03/043581 provide a long list of such compounds as potential candidates for FXR-activating ligands.

B. Examples of Known FXR-Activating Ligands

A growing list of known FXR-specific ligands includes chenodeoxycholic acid (CDCA), 6ECDCA, GW4064, 6α-MeCDCA, 6α-PrCDCA, fexaramine, lithocholic acid (LCA), cholate (CA), ursodeoxycholic acid (UDCA), and deoxycholic acid (DCA) (see, e.g., Pellicciari et al., *J. Med. Chem.*, 45: 3569-3572, 2002). Among the FXR ligands, those with a lower EC50, e.g., no greater than 5 μM, preferably no greater than 2 μM, more preferably no greater than 1.5 μM, and most preferably no greater than 1 μM, when tested in a cell-free assay or a cell-based transactivation assay using a human or rat FXR, are effective for the practice of this invention. An FXR ligand exhibiting an $EC_{50}$ no greater than 0.2 μM or no greater than 0.1 μM, such as 6ECDCA, is particularly effective for the treatment method of this invention (see, e.g., Fiorucci et al., *Gastroenterology* 127: 1497-1512, 2004). These FXR ligands can be chemically synthesized according to well known methods or some of them can be purchased from commercial suppliers such as Sigma-Aldrich (USA), Erregierre (Italy), and Hengchanlong Pharmaceuticals (China).

IV. Pharmaceutical Compositions and Administration

The present invention also provides pharmaceutical compositions comprising an effective amount of an FXR ligand for treating fibrosis in both prophylactic and therapeutic applications. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, intramuscular, intravenous, or intraperitoneal. The referred routes of administering the pharmaceutical compositions are oral, subcutaneous, and intravenous at daily doses of about 0.01-5000 mg, preferably 5-500 mg, of the FXR ligand for a 70 kg adult human per day. The appropriate dose may be administered in a single daily dose or as divided doses presented at appropriate intervals, for example as two, three, four, or more subdoses per day.

For preparing pharmaceutical compositions containing an FXR ligand, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an FXR ligand. In tablets, the active ingredient (FXR ligand) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of FXR ligand. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of an FXR ligand with encapsulating material as a carrier providing a capsule in which the FXR ligand (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an FXR ligand) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an FXR ligand) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 and 8.

The pharmaceutical compositions containing FXR ligands can be administered for prophylactic and/or therapeutic treatments. In therapeutic applications, compositions are administered to a patient already suffering from fibrosis of an organ where FXR is expressed, in an amount sufficient to prevent, cure, reverse, or at least partially slow or arrest the symptoms of the disease and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the compound per day for a 70 kg patient, with dosages of from about 5 mg to about 500 mg of the compound per day for a 70 kg patient being more commonly used.

In prophylactic applications, pharmaceutical compositions containing FXR ligands are administered to a patient susceptible to or otherwise at risk of developing fibrosis in an organ where FXR is expressed, e.g., liver, kidney, intestine, etc., in an amount sufficient to delay or prevent the onset of the fibrostic symptoms. Such an amount is defined to be a "prophylactically effective dose." In this use, the precise amounts of the FXR ligand again depend on the patient's state of health and weight, but generally range from about 0.1 mg to about 2,000 mg for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of an FXR ligand sufficient to effectively inhibit fibrosis in the patient, either therapeutically or prophylatically.

V. Kits

The invention also provides kits for preventing, treating, or reversing fibrosis according to the method of the present invention. The kits typically include a pharmaceutical composition that contains an effective amount of a ligand specific for FXR and capable of stimulating FXR's transcriptional activity, as well as informational material containing instructions of how to dispense the pharmaceutical composition, including description of the type of patients who may be treated (e.g., a person at risk of developing liver fibrosis in an organ where FXR is expressed but not suffering from a cholestatic condition), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially similar results.

Example 1: FXR Ligand-Mediated Suppression of Collagen Type α1 Expression in Hepatic Stellate Cells (HSC)

Liver fibrosis leading eventually to cirrhosis is a scarring process of the liver that includes components of both increased fibrogenesis and wound contraction. Hepatic stellate cells (HSCs) are recognized as the main cell type responsible for liver fibrogenesis. In chronic liver disease, HSCs acquire an "activated" phenotype, which includes increased proliferation, contractility, fibrogenesis, matrix degradation, chemotaxis, and cytokine release (Friedman, *J. Biol. Chem.* 275: 2247-2250, 2000). The current paradigm postulates that the activated state of HSCs is achieved through the transformed microenvironment, which is supported in part by the growth factors Platelet-Derived Growth Factor (PDGF) and Transforming Growth Factor (TGF)-β, reactive oxygen intermediates released by hepatocytes and by the fibrillar matrix generated by previously activated HSCs, as well as in response to stimulation with thrombin and its type I receptor (proteinase activate receptor 1, or PAR-1) (Fiorucci, et al., *Hepatology*, 39: 365-75, 2004). The α-1 type of collagen I (α1) represents the major collagen subtype found in the normal and cirrhotic liver (Friedman, *J. Biol. Chem.*, 275: 2247-2250, 2000). Collagen α1 is generated in the fibrotic and cirrhotic liver by activated HSCs.

Bile acids act as signaling molecules that regulate their own biosynthesis and transport by binding to and activating the farnesoid X receptor (FXR), also known as NR1H4 and the bile acid receptor (BAR), a nuclear receptor expressed in tissues exposed to bile acids, such as liver, intestine, gallbladder, and kidney. FXR alters transcription by binding DNA sequences composed of two inverted repeats separated by one nucleotide (IR-1) as a heterodimer with the 9-cis-retinoic acid (9-cis-RA) receptor (RXR, also known as NR2B1). In hepatocytes, upon activation, FXR initiates a transcription of a cohort of genes that function to decrease the concentration of bile acids within the hepatocyte. Specifically, activated FXR induces the expression of the genes encoding BSEP, multidrug resistance protein 3 (MDR3; ABCB4), and MRP2. In addition, activation of FXR by both its naturally occurring ligands (e.g., chenodeoxycholic acid, CDCA) and synthetic ligands (e.g., 6ECDCA and GW4064) leads to a feedback repression of $Na^+$/taurocholate co-transporting polypeptide (NTCP; SLC10A1), CYP7A1 and CYP8B1. These genes encode cholesterol 7α-hydroxylase and sterol 12α-hydroxylase, both of which are central to the synthesis of bile acids from cholesterol. The FXR-dependent suppression of CYP7A1 is mediated by the transcriptional repressor, short heterodimer partner (SHP; NR0B2), an atypical nuclear receptor that lacks a DNA-binding domain. Thus, upon activation, FXR directly induces expression of SHP, which in turn interacts with liver receptor homolog-1 (LRH-1; NR5A2), a known positive regulator of CYP7A1 and represses its transcriptional activity. Studies performed in mice harboring a disrupted SHP gene have confirm the importance of the FXR-SHP-LRH-1 cascade in suppression of CYP7A1 (see, e.g., Forman et al., *Cell* 81: 687-693, 1995; Seol et al., *Mol. Endocrinol.* 9: 72-85, 1995; Sinal et al., *Cell* 102: 731-744, 2000; Ananthanarayanan et al., *J. Biol. Chem.*, 276: 28857-28865, 2001; Holt et al., *Genes Dev.*, 17: 1581-91, 2003; Kast et al., *J. Biol. Chem.*, 277: 2908-2915, 2002; Goodwin et al., *Mol. Cell* 6: 517-526, 2000; and Lu et al., *Mol. Cell* 6: 507-515, 2000).

The goals of the study presented hereafter are: 1) to demonstrate whether HSCs express FXR; 2) to demonstrate whether FXR ligands modulate collagen α1 expression and synthesis in vitro; and 3) to define molecular intermediates of this effect. Two types of HSCs were used in this study, either freshly isolated cells in primary cultures or an immortalized cell line (HSC-T6) obtained from rat HSCs.

Figure 1B:
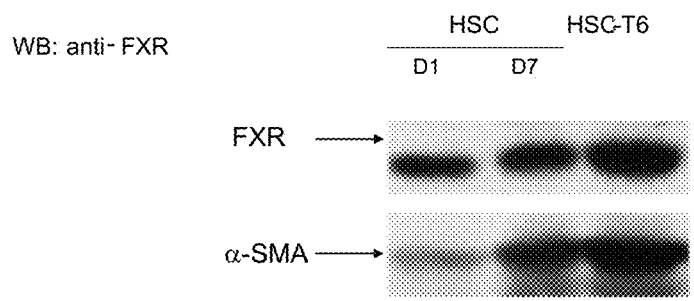
FIG. 1B shows the expression of FXR in the primary cultures of HSC-TS at protein level by Western blot analysis.

The results as shown in FIGS. 1A and 1B demonstrate that both primary cultures of HSCs and HSC-T6 express FXR, as assessed by measuring mRNA (FIG. 1B) by reverse transcription polymerase chain reaction (RT-PCR) and protein by Western blot analysis. (FIG. 1B) FIG. 1B demonstrates that the amount of FXR in HSC increases over time during culture and its increase parallels the expression of α-smooth muscle actin (αSMA), a marker of HSC differentiation into myofibroblast-like cells. Thus, while HSCs acquire their differentiated phenotype, they also express FXR. Consistent with this, FXR expression was also detected in HSC-T6.

It was then assessed whether HSCs express genes that are known FXR transcriptional targets. As shown in FIG. 2A, NTCP, BSEP, CYP7A1, and SHP expression was detected in HSC. Furthermore, as shown in FIG. 2 Panel b, the expression of these genes in HSC is regulated by FXR ligands. The quantitative RT-PCR shown in FIG. 2B illustrates that exposure to 6ECDCA, a synthetic FXR ligand, (at a concentration of 1 µM) and to CDCA, a natural FXR ligand, (at a concentration of 20 µM) results in a 2-fold increase of SHP and BSEP mRNA and a 50-70% reduction of NTCP and CYP7A1 mRNA.

As illustrated in FIG. 3A, exposure of HSCs to FXR ligands 6ECDCA (1 µM), CDCA (20 µM), and GW4064 (100 µM) reduces the expression of type I collagen as measure by assessing α1 mRNA expression by RT-PCR and quantitative RT-PCR. These observations have been confirmed by Northern blot analysis, as shown in FIG. 3B.

The inhibitory effect FXR ligands exert on synthesis of α1 collagen in vitro is not related to inhibition of HSC proliferation or induction of HSC death, since, as illustrated in FIGS. 4A, 4B and 4C, 6ECDCA does not prevent HSC proliferation induced by thrombin, PDGF, and TGF$^{β1}$, as assessed by determining [$^3$H]-thymidine incorporation (FIGS. 4A and 4B) or cell counting (FIG. 4C). Furthermore, FXR ligand exposure does not result in any HSC apoptosis (FIG. 4D).

As illustrated in FIGS. 5A and 5B, FXR ligands also inhibit collagen α1 release as measured by determining hydroxyproline concentrations in cell supernatants, a measure of collagen release from HSCs.

Figure 6A:
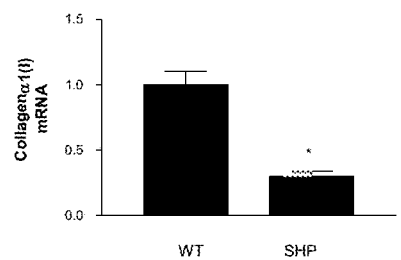
FIG. 6A shows that SHP overexpression in HSC-T6 abrogates α1 expression on resting HSC-T6, as measured by QRT-PCR.
Figure 6B:
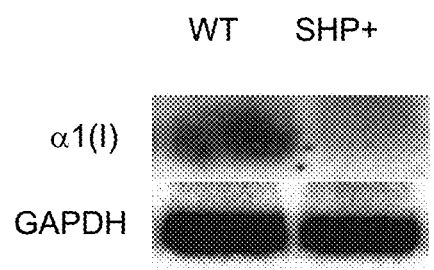
FIG. 6B shows results of Northern blot analysis.
Figure 6C:
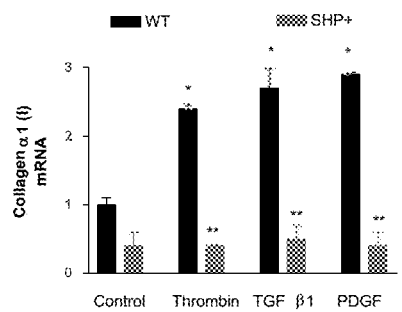
FIG. 6C shows that SHP overexpression in HSC-T6 prevents α1 induction caused by thrombin, TGFβ1, and PDGF.

Because the α1 gene lacks an IR that might be used by FXR to bind the α1 promoter, we have investigated mediators involved in the inhibition of α1 expression induced by FXR ligands in HSC and found evidence that SHP induction is strictly required by FXR ligands in order to inhibit α1 expression. Indeed, as illustrated in FIGS. 6A, 6B and 6C, SHP overexpression in HSC-T6 abrogates α1 expression on resting HSC-T6 as measured by QRT-PCR (FIG. 6A) and Northern blot analysis (FIG. 6B), and prevents α1 induction caused by thrombin, TGFβ1 and PDGF. (FIG. 6C)

Figure 7A:
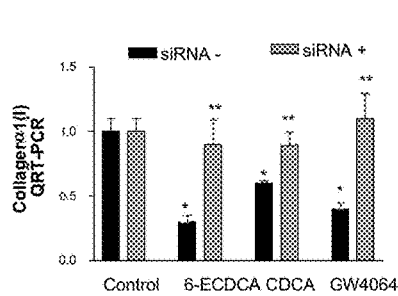
FIG. 7A shows that abrogation of SHP expression, by specific small interference RNA (siRNA), reverses α1 mRNA inhibition caused by FXR ligands.
Figure 7C:
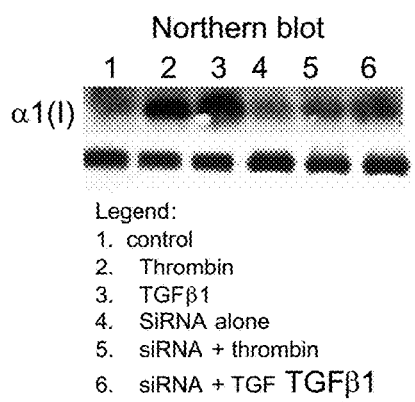
FIG. 7C shows results of Northern blot analysis confirming the effect of SHP on α1 mRNA.
Figure 7B:
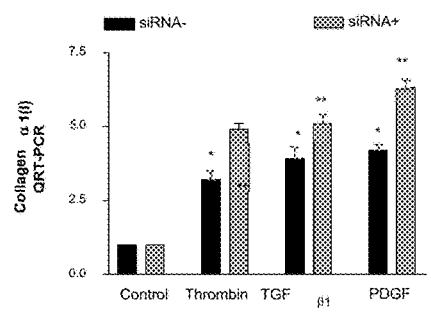
FIG. 7B shows that silencing of SHP also prevents inhibition of α1 expression induced by FXR ligands on HSCs treated with mitogenic factors such as thrombin, TGFβ and PDGF.

In contrast, as illustrated in FIGS. 7A 7B and 7C, abrogation of SHP expression by specific small interference RNA (siRNA), reversed α1 mRNA inhibition caused by FXR ligands (FIG. 7A). Silencing SHP also prevented inhibition of α1 expression induced by FXR ligands in HSCs treated with mitogenic factors such as thrombin, TGF and PDGF (FIG. 7B). These data were confirmed by Northern blot analysis. (FIG. 7C)

In summary, data presented herein demonstrate that HSCs, the cells that produce collagen in the liver and are responsible for liver fibrosis, express FXR and that exposure of these cells to natural or synthetic ligands of FXR down-regulates collagen α1 mRNA and secretion by a mechanism that involves the induction of SHP.

Materials and Methods

Real Time PCR

Quantitation of the expression genes was performed by Real-Time Polymerase Chain Reaction (Q-RTPCR). Total RNA was isolated (TRIzol reagent-Invitrogen) from rat hepatic stellate cells (HSC) or T6 cell line starved for 24 h and stimulated with FXR ligand 6ECDCA 1 µM for 18 hours. One µg RNA was purified of the genomic DNA by DNaseI treatment (Invitrogen) for 15 min at room temperature. The DNaseI is inactivated at 95° C. for 5 minutes in presence of 2.5 mM EDTA. The RNA was random reverse-transcribed with Superscript III (Invitrogen) in 20 µl reaction volume. One hundred ng template was used in 25 µl final volume reaction of Real-Time PCR contained the following reagents: 0.3 µM of each primer and 12.5 µl of 2×SYBR Green PCR Master MIX (Bio-Rad). All reactions were performed in triplicate and the thermal cycling conditions were: 2 minutes at 95° C., followed by 50 cycles of 95° C. for 10 seconds, and 60° C. for 30 seconds in iCycler iQ instrument (Biorad, Hercules, Calif.). The mean value of the replicates for each sample was calculated and expressed as cycle threshold (CT: cycle number at which each PCR reaction reaches a predetermined fluorescence threshold, set within the linear range of all reactions). The amount of gene expression was then calculated as the difference ($\Delta C_T$) between the $C_T$ value of the sample for the target gene and the mean $C_T$ value of that sample for the endogenous control (Actin). Relative expression was calculated as the difference ($\Delta\Delta C_T$) between the $\Delta C_T$ values of the test sample and of the control sample (WT) for each target gene. The relative quantitation value was expressed and shown as 2-$\Delta\Delta C_T$A11 PCR primers were designed using software PRIMER3-OUTPUT using published sequence data from the NCBI database. Primers: Rat SHP: 5' cctggagcagccctcgt 3' (SEQ ID NO: 1) and 5' aacactgtatgcaaaccgagga 3' (SEQ ID NO: 2); Rat FXR: 5' tggactcatacagcaaacagaga 3' (SEQ ID NO: 3) and 5' gtctgaaaccctggaagtctttt 3' (SEQ ID NO: 4); Rat Col1A1: 5' tctccaagaggcagggttc 3' (SEQ ID NO: 5) and 5' ggttagcttcggctcatgc 3' (SEQ ID NO: 6); Rat c-Jun: 5' gaagcagagcatgaccttga 3' (SEQ ID NO: 7) and 5' gacgtgagaaggtcgagtt 3 (SEQ ID NO: 8)'; Rat JunD: 5' atcttgggctgctcaaactc 3' (SEQ ID NO: 9) and 5' gccaccttagggtagaggaa 3' (SEQ ID NO: 10); Rat Actin: 5' ttaatgtcacgcacgatttc 3'(SEQ ID NO: 11) and 5' taccactggcattgttgatgg 3' (SEQ ID NO: 12).

Northern Blot Analysis

Levels of Collagen I alpha I were determined by Northern blot analyses of total RNA samples prepared from primary hepatic stellate cells (HSC), T6 and HepG2 cell lines. For this purpose, 10 µg total RNA was resolved by gel electrophoresis (1% agarose containing 0.98 M formaldehyde). Immediately after electrophoresis the RNA was transferred to a positively charged Nylon membrane (Amersham Life Sciences crop.). The transferred RNA was cross-linked to the membrane by UV light. The membrane was prehybridized for 4 hours in 6×SSC and 2% SDS and subsequently hybridized at 65° C. for 20 h with 32$^P$-labeled probes for collagen I alpha I or GAPDH (as internal control). Hybridized membranes were washed at a final stringency of 1×SSC, 1.0% SDS at 65° C. and exposed to Kodak AR-2 film at −80° C. The data are expressed relative to the internal GAPDH.

Western Blot Analysis

Confluent cultures of HSC or T6 cell lines were serum starved for 48 h and then incubated for 18 h at 37° C. in DMEM with or without either Thrombin (10 units/ml), 6ECDCA (1 µM). Total lysates were prepared by cells solubilization in SDS Laemmly sample buffer (62.5 mM Tris-HCl, pH 6.8, 10% glycerol 2% SDS, 0.015% Bromophenol Blue), and 3-4×105 cells were electrophoresed on 10% polyacrylamide gels. Separated proteins were then transferred to nitrocellulose membranes (BioRad), and the membranes were probed with primary antibodies to c-Jun, JunD, SHP, FXR, αSMA (Santa Cruz Biotechnology). The anti-immunoglobulin G horseradish peroxidase conjugate (Bio-Rad) was added as the secondary antibody, and specific protein bands were visualized using enhanced chemiluminescence (ECL; Amersham corp.) following the manufacturer's suggested protocol.

Co-Immunoprecipitation Assay

To prepare extracts for immunoprecipitation, primary HSC cells, or T6 and T6 over-expressing SHP cells were first washed three times with ice cold PBS and then lysed by sonication in E1A buffer (50 mM Hepes, pH 7, 250 mM NaCl, 0.1% NP-40, 5 mM EDTA, 1 mM DTT, 1 mM PhenylMethylSulfonyl Fluoride, 1 mg/ml leupeptin, 1 mg/ml aprotinin and 1 mg/ml pepstatin A). The lysates were clarified from membrane detrites by centrifugation at 13,000 g for 10 min, and the protein concentrations in the supernatant extracts was adjusted to 1 mg/ml. From one to four mg total proteins or $10^7$ cells lysates were immunoprecipitated with anti SHP, anti JunD or anti c-Jun (Santa Cruz Biotechnology, Santa Cruz, Calif.) or anti CD28 as uncorrelated antibody (control) overnight at +4° C. in the presence of 10 µl protein A sepharose (Amersham Pharmacia Biotechnology, Piscataway, N.J.). The resultant immunoprecipitate was washed 5 times with E1A and then subjected to SDS-PAGE and immunoblotted with antibodies (reverse) used in immunoprecipitates.

Transduction of the Viral Vector Mediated SHP Gene in T6 Cells

The SHP coding sequence was cloned from rat primary hepatocyte. Briefly one µg total RNA was retro-trascribed with SuperScript III reverse trascriptase (Invitrogen) in 20 µl reaction using 0.3 µM Random Hexamers. Two hundred cDNA template was used to amplify the coding sequence of SHP with Pfu DNA polimerase (Stratagene) in 50 µl PCR reaction using specific primers 5'-CATGAGCACCAGC-CAACCAG-3' (SEQ ID NO: 13) and 5'-CTGGAACAGGT-CACCTGAGC-3 (SEQ ID NO: 14). SHP coding sequence was first cloned in pCR2.1 vector (TOPO-TA cloning—Invitrogen) and then sub-cloned in retroviral vector PINCO. 293T modified packaging cells (ΦNX) were cultured in DMEM medium with 10% FBS and calcium phosphate transiently transfected with PINCO-SHP chimera and PINCO alone as negative control. 48 hours' post-transfection the supernatant viral was recuperated and used to infect T6 cells. PINCO vector leads the EGFP (Emerald Green Fluorescence Protein) gene that allows the separation of the infected cells (green) from non-infected cells. A pure population of the T6 cells expressing SHP was obtained by FACS (Fluorescence Activated Cell Sorter) separation. The SHP expression was detected by Western Blot analysis.

Example 2: Administration of FXR Ligands Results in Reduced Fibrosis in Bile Duct Ligated (BDL) Rats BDL is a model of chronic cholestasis. In this model, however, progressive liver fibrosis leads to the development of cirrhosis 3-4 weeks after ligation and it is therefore also used as a model of liver fibrosis (Kountouras et al., Br. J. Exp. Pathol., 65: 305-311, 1984). Because this model allows us to test the effect of anti-fibrotic remedies, we administered rats 3 days after BDL with 6ECDCA at the dose of 1 and 3 mg/kg per os per day for 2 weeks. The protocol's study was approved by the Animal Study Committee of the University of Perugia. Hepatic fibrosis was induced in 8-9 weeks old male Wistar rats (Charles River, Monza, Italy) by BDL. BDL was performed as originally described by Kountouras et al. (Br. J. Exp. Pathol. 65: 305-311; 1984). One week after BDL, rats were randomized to receive one of the following treatments, placebo (subcutaneous injection of 100 µL PBS) or 6ECDCA at the doses 1 and 3 mg/kg/day by oral route. Animals were then followed for 3 weeks.

At the end of the study surviving rats were sacrificed under pentobarbital sodium anesthesia (50 mg/kg i.p) and terminally bled via cardiac puncture. The blood was centrifuged at 7250 g for 20 minutes at 4° C.; the resultant serum was stored at −20° C. until analysis (a maximum of 2 weeks). At the time of death, the bile duct ligature was confirmed to be intact with proximal dilatation of the common bile duct. After weight determination, specimens of livers were snap frozen in liquid nitrogen and stored at −70° C. for subsequent analysis. For histologic examination portions of the right and left liver lobes (10-15 mg/each) from each animal were fixed in 10% formalin, embedded in paraffin, sectioned, and stained with hematoxylin and eosin or Sirius red. For Sirius red staining, the sections were incubated for 30 minutes in 0.1% Sirius red F3B (Sigma Chemical Co.) containing saturated picric acid and 0.1% Fast Green. After rinsing twice with distilled water, sections were briefly dehydrated with 70% ethanol and coverslipped. Collagen surface density from liver samples was quantified using a computerized image analysis system as described previously (Image Acquisition System Ver. 005, Delta Sistemi, Rome, Italy). The surface density of collagen in blinded specimens was measured at a video screen display magnification according to the method described by Rockey and Chung (Rockey, D. C., Chung, J. J. *J. Clin. Invest.* 98: 1381-1388, 1996) and expressed as a percent (the ratio of collagen surface area per total analyzed field surface). The average of the score taken from 10 random fields was used to generate a single score for each animal's liver.

Figure 8A:
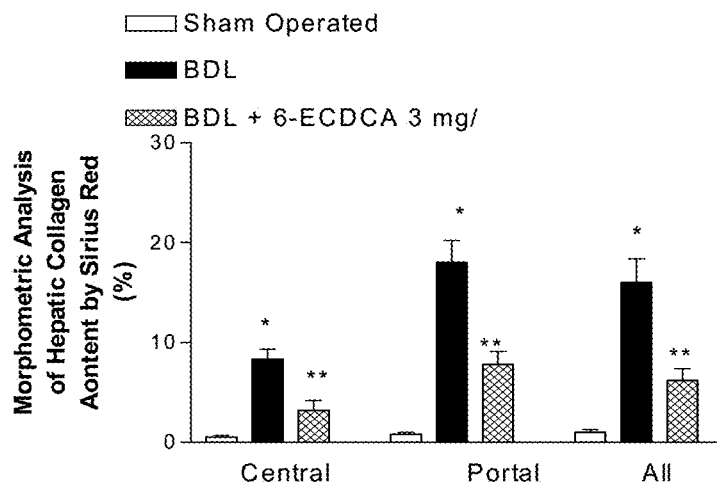
FIG. 8A shows the levels of collagen deposition, hydroxyproline, and α1 collagen mRNA in the livers of BDL rats treated or untreated with 6ECDCA.
Figure 8B:
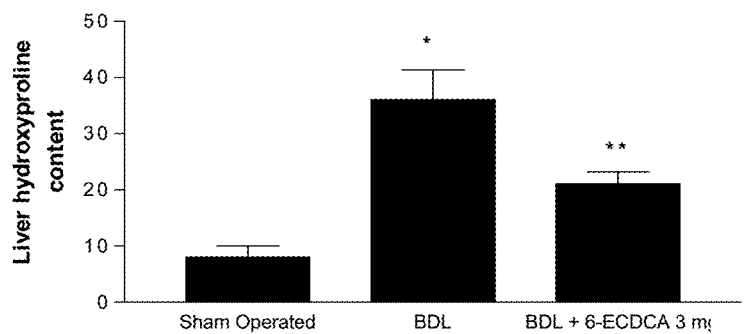
FIG. 8B shows the levels of hydroxyproline in the livers of BDL rats treated or untreated with 6ECDCA.
Figure 8C:
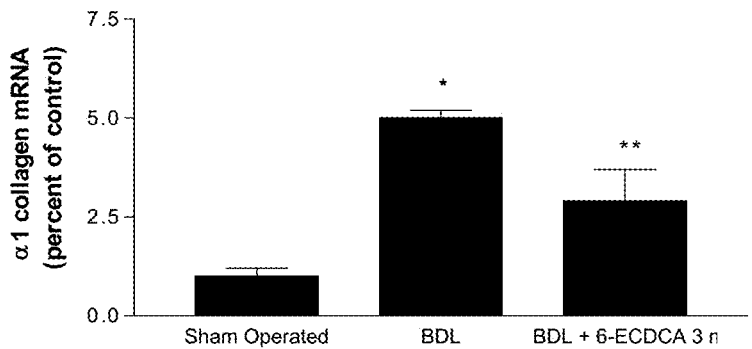
FIG. 8C shows the levels of α1 collagen mRNA in the livers of BDL rats treated or untreated with 6ECDCA.

As illustrated in FIGS. 8A, 8B and 8C, in vivo delivery of 6ECDCA resulted in significant reduction of liver collagen deposition as measured by scoring of Sirius-red staining (FIG. 8A), liver hydroxyproline content (FIG. 8B), and liver α1 mRNA by RT-PCR (FIG. 8C). Quantitative analysis of Sirius Red stained collagen in the liver demonstrated a reduction in liver collagen content by 62% after treatment with 6ECDCA. In FIG. 8 data are mean±SE; * indicates P<0.01 versus sham operated and **, P<0.01 versus BDL. "Central" and "portal" refer to the central vein and the portal tract areas, as well as the parenchymal area immediately surrounding these spaces. "All" refers to all hepatic areas, as visualized under low magnification.

Example 3: Administration of FXR Ligands to Inhibit Fibrosis

The present invention can be practiced according to the following example. A 58-year old female patient, weighing about 60 kg, suffers from chronic Hepatitis C Virus (HCV) infection and is seeking treatment to inhibit development and progression of liver fibrosis. The patient's blood serum levels of alkaline phosphatase, GGT, and 5' nucleotidase are considered to fall within a range that is not indicative of a cholestatic condition. After assessment of liver fibrosis status and staging by performing liver biopsy and/or measurement of non-invasive serum markers, tablets containing 6ECDCA are prescribed to the patient for oral administration on a twice-per-day schedule. A total of 300 mg 6ECDCA is taken each day. The patient is on this schedule for the remainder of her life. The development or progression of liver fibrosis can be monitored based on measuring serum markers or analyzing liver biopsy.

All patents, patent applications, and other publications cited in this application are incorporated by reference in the entirety for all purposes.

What is claimed is:

1. A method of treating liver fibrosis associated with alcoholic liver disease (ALD) in a human not suffering from a cholestatic condition in need thereof the method comprising the step of administering to the human 6-ethyl-chenodeoxycholic acid at a daily dose of 5-500 mg orally.

2. The method of claim 1 wherein the cholestatic condition is defined as having abnormally elevated serum levels of alkaline phosphatase, γ-glutamyltranspeptidase (GGT), and 5' nucleotidase.

3. The method of claim 2, wherein the cholestatic condition is further defined as presenting with at least one clinical symptom.

4. The method of claim 3, wherein the symptom is itching (pruritus).

5. The method of claim 1, wherein the cholestatic condition is selected from the group consisting of primary biliary cirrhosis, primary sclerosing cholangitis, drug-induced cholestasis, hereditary cholestasis, and intrahepatic cholestasis of pregnancy.

6. The method of claim 1, wherein the human is not suffering from a cholestatic condition associated with a disease or condition selected from the group consisting of primary liver and biliary cancer, metastatic cancer, sepsis, chronic total parenteral nutrition, cystic fibrosis, and granulomatous liver disease.

* * * * *